US010426456B2

(12) United States Patent
Pamichev et al.

(10) Patent No.: US 10,426,456 B2
(45) **Date of Patent: *Oct. 1, 2019**

(54) METHOD AND APPARATUS FOR RE-ATTACHING THE LABRUM TO THE ACETABULUM, INCLUDING THE PROVISION AND USE OF A NOVEL SUTURE ANCHOR SYSTEM

(71) Applicant: Pivot Medical, Inc., Sunnyvale, CA (US)

(72) Inventors: Chris Pamichev, Cupertino, CA (US); J. Brook Burley, Mountain View, CA (US); Julian Nikolchev, Portola Valley, CA (US); James Flom, San Carlos, CA (US)

(73) Assignee: Pivot Medical, Inc., Sunnyvale, CA (US)

( * ) Notice: Subject to any disclaimer, the term of this patent is extended or adjusted under 35 U.S.C. 154(b) by 157 days.

This patent is subject to a terminal disclaimer.

(21) Appl. No.: 15/277,130

(22) Filed: Sep. 27, 2016

(65) Prior Publication Data

US 2017/0231616 A1 Aug. 17, 2017

Related U.S. Application Data

(63) Continuation of application No. 13/642,168, filed as application No. PCT/US2011/021173 on Jan. 13, (Continued)

(51) Int. Cl.

| | |
|---|---|
| ***A61B 17/04*** | (2006.01) |
| ***A61B 17/16*** | (2006.01) |
| ***A61B 17/17*** | (2006.01) |

(52) U.S. Cl.

CPC ...... *A61B 17/0401* (2013.01); *A61B 17/1604* (2013.01); *A61B 17/1666* (2013.01); (Continued)

(58) Field of Classification Search

CPC ........ A61B 17/0401; A61B 2017/0409; A61B 2017/0412; A61B 2017/0414; (Continued)

(56) References Cited

U.S. PATENT DOCUMENTS

| | | | |
|---|---|---|---|
| 919,138 | A | 4/1909 | Drake et al. |
| 2,416,260 | A | 2/1947 | Karle |

(Continued)

FOREIGN PATENT DOCUMENTS

| | | |
|---|---|---|
| EP | 0 232 049 | 8/1987 |
| EP | 0 241 240 | 10/1987 |

(Continued)

*Primary Examiner* — Robert A Lynch
(74) *Attorney, Agent, or Firm* — Pandiscio & Pandiscio

(57) ABSTRACT

Apparatus for securing a first object to a second object, the apparatus comprising: an elongated body having a distal end, a proximal end, and a lumen extending between the distal end and the proximal end, the lumen comprising a first section and a second section, the first section of the lumen being disposed distal to the second section of the lumen, and with the first section of the lumen having a wider diameter than the second section of the lumen; at least one longitudinally-extending slit extending through the side wall of the elongated body and communicating with the lumen, the at least one longitudinally-extending slit having a distal end and a proximal end, with the distal end of the at least one longitudinally-extending slit being spaced from the distal end of the elongated body; and an elongated element extending through the lumen of the elongated body.

64 Claims, 42 Drawing Sheets

80
85
75
95
105
10

Related U.S. Application Data

2011, now Pat. No. 9,451,943, which is a continuation-in-part of application No. 12/839,246, filed on Jul. 19, 2010, now Pat. No. 9,179,905.

(60) Provisional application No. 61/326,709, filed on Apr. 22, 2010, provisional application No. 61/271,205, filed on Jul. 17, 2009.

(52) U.S. Cl.
CPC .. *A61B 17/1746* (2013.01); *A61B 2017/0409* (2013.01); *A61B 2017/0412* (2013.01); *A61B 2017/0414* (2013.01); *A61B 2017/0424* (2013.01); *A61B 2017/0438* (2013.01); *A61B 2017/0445* (2013.01); *A61B 2017/0458* (2013.01)

(58) Field of Classification Search
CPC .... A61B 2017/0422; A61B 2017/0424; A61B 2017/0427; A61B 2017/043; A61B 2017/0432; A61B 2017/0438; A61B 2017/0448; A61B 2017/0456; A61B 2017/0458
See application file for complete search history.

(56) References Cited

U.S. PATENT DOCUMENTS 2,579,192 A 12/1951 Kohl
2,808,055 A 10/1957 Thayer
3,566,739 A 3/1971 Lebar
3,708,883 A 1/1973 Flander
4,408,938 A 10/1983 Maguire
4,484,570 A 11/1984 Sutter et al.
4,492,226 A 1/1985 Belykh et al.
4,590,928 A 5/1986 Hunt et al.
4,605,414 A 8/1986 Czajka
4,632,100 A 12/1986 Somers et al.
4,708,132 A 11/1987 Silvestrini
4,741,330 A 5/1988 Hayhurst
4,778,468 A 10/1988 Hunt et al.
4,779,616 A 10/1988 Johnson
4,870,957 A 10/1989 Goble et al.
4,871,289 A 10/1989 Choiniere
4,927,421 A 5/1990 Goble et al.
5,037,422 A 8/1991 Hayhurst et al.
5,046,513 A 9/1991 Gatturna et al.
5,176,682 A 1/1993 Chow
5,207,679 A 5/1993 Li
5,209,753 A 5/1993 Biedermann et al.
5,224,946 A 7/1993 Hayhurst et al.
5,226,426 A 7/1993 Yoon
5,236,445 A 8/1993 Hayhurst et al.
5,268,001 A 12/1993 Nicholson et al.
5,324,308 A 6/1994 Pierce
5,330,442 A 7/1994 Green et al.
5,336,240 A 8/1994 Metzler et al.
5,354,298 A 10/1994 Lee et al.
5,364,407 A 11/1994 Poll
5,383,905 A 1/1995 Golds et al.
5,405,352 A 4/1995 Weston
5,411,523 A 5/1995 Goble
5,417,712 A 5/1995 Whittaker et al.
5,423,860 A 6/1995 Lizardi et al.
5,464,427 A 11/1995 Curtis et al.
5,472,452 A 12/1995 Trott
5,480,403 A 1/1996 Lee et al.
5,486,197 A 1/1996 Le et al.
5,489,210 A 2/1996 Hanosh
5,499,991 A 3/1996 Garman et al.
5,501,683 A 3/1996 Trott
5,501,692 A 3/1996 Riza
5,501,695 A 3/1996 Anspach, Jr. et al.
5,514,159 A 5/1996 Matula et al.
5,522,844 A 6/1996 Johnson
5,522,845 A 6/1996 Wenstrom, Jr.
5,534,012 A 7/1996 Bonutti
5,545,180 A 8/1996 Le et al.
5,562,683 A 10/1996 Chan
5,562,687 A 10/1996 Chan
5,569,306 A 10/1996 Thal
5,571,139 A 11/1996 Jenkins, Jr.
5,584,835 A 12/1996 Greenfield
5,601,557 A 2/1997 Hayhurst
5,601,558 A 2/1997 Torrie et al.
5,611,515 A 3/1997 Benderev et al.
5,630,824 A 5/1997 Hart
5,632,748 A 5/1997 Beck, Jr. et al.
5,643,292 A 7/1997 Hart
5,643,321 A 7/1997 McDevitt
5,645,589 A 7/1997 Li
5,647,874 A 7/1997 Hayhurst
5,649,963 A 7/1997 McDevitt
5,658,313 A 8/1997 Thal
5,662,658 A 9/1997 Wenstrom, Jr.
5,665,112 A 9/1997 Thal
5,681,320 A 10/1997 McGuire
5,681,333 A 10/1997 Burkhart et al.
5,683,419 A 11/1997 Thal
5,690,649 A 11/1997 Li
5,702,215 A 12/1997 Li
5,702,397 A 12/1997 Goble et al.
5,702,422 A 12/1997 Stone
5,707,395 A 1/1998 Li
5,709,708 A 1/1998 Thal
5,713,903 A 2/1998 Sander et al.
5,716,368 A 2/1998 de la Torre et al.
5,720,765 A 2/1998 Thal
5,725,529 A 3/1998 Nicholson et al.
5,725,541 A 3/1998 Anspach, III et al.
5,728,136 A 3/1998 Thal
5,741,300 A 4/1998 Li
5,746,752 A 5/1998 Burkhart
5,746,753 A 5/1998 Sullivan et al.
5,755,728 A 5/1998 Maki
5,782,862 A 7/1998 Bonutti
5,782,863 A 7/1998 Bartlett
5,782,864 A 7/1998 Lizardi
5,791,899 A 8/1998 Sachdeva et al.
5,797,963 A 8/1998 McDevitt
5,814,071 A 9/1998 McDevitt et al.
5,814,072 A 9/1998 Bonutti
5,814,073 A 9/1998 Bonutti
5,843,127 A 12/1998 Li
5,845,645 A 12/1998 Bonutti
5,849,004 A 12/1998 Bramlet
5,891,168 A 4/1999 Thal
5,906,624 A 5/1999 Wenstrom, Jr.
5,910,148 A 6/1999 Reimels et al.
5,911,721 A 6/1999 Nicholson et al.
5,928,244 A 7/1999 Tovey et al.
5,935,129 A 8/1999 McDevitt et al.
5,935,134 A 8/1999 Pedlick et al.
5,935,149 A 8/1999 Ek
5,948,000 A 9/1999 Larsen et al.
5,948,001 A 9/1999 Larsen
5,957,953 A 9/1999 DiPoto et al.
5,968,044 A 10/1999 Nicholson et al.
5,980,558 A 11/1999 Wiley
5,980,559 A 11/1999 Bonutti
5,993,459 A 11/1999 Larsen et al.
6,010,514 A 1/2000 Burney et al.
6,022,360 A 2/2000 Reimels et al.
6,041,485 A 3/2000 Pedlick et al.
6,045,573 A 4/2000 Wenstrom, Jr. et al.
6,045,574 A 4/2000 Thal
6,056,772 A 5/2000 Bonutti
6,077,277 A 6/2000 Mollenauer et al.
6,086,608 A 7/2000 Ek et al.
6,099,538 A 8/2000 Moses et al.
6,099,547 A 8/2000 Gellman et al.
6,117,144 A 9/2000 Nobles et al.
6,143,017 A 11/2000 Thal

(56) References Cited

U.S. PATENT DOCUMENTS

| | | | |
|---|---|---|---|
| 6,149,669 | A | 11/2000 | Li |
| 6,159,234 | A | 12/2000 | Bonutti et al. |
| 6,200,329 | B1 | 3/2001 | Fung et al. |
| 6,221,107 | B1 | 4/2001 | Steiner et al. |
| 6,231,592 | B1 | 5/2001 | Bonutti et al. |
| 6,241,732 | B1 | 6/2001 | Overaker et al. |
| 6,245,081 | B1 | 6/2001 | Bowman et al. |
| 6,245,082 | B1 | 6/2001 | Gellman et al. |
| 6,312,448 | B1 | 11/2001 | Bonutti |
| 6,319,252 | B1 | 11/2001 | McDevitt et al. |
| 6,319,269 | B1 | 11/2001 | Li |
| 6,475,230 | B1 | 11/2002 | Bonutti et al. |
| RE37,963 | E | 1/2003 | Thal |
| 6,506,190 | B1 | 1/2003 | Walshe |
| 6,517,579 | B1 | 2/2003 | Paulos et al. |
| 6,520,980 | B1 | 2/2003 | Foerster |
| 6,524,316 | B1 | 2/2003 | Nicholson et al. |
| 6,527,794 | B1 | 3/2003 | McDevitt et al. |
| 6,527,795 | B1 | 3/2003 | Lizardi |
| 6,544,281 | B2 | 4/2003 | ElAttrache et al. |
| 6,547,800 | B2 | 4/2003 | Foerster et al. |
| 6,547,807 | B2 | 4/2003 | Chan et al. |
| 6,562,071 | B2 | 5/2003 | Järvinen |
| 6,575,976 | B2 | 6/2003 | Grafton |
| 6,575,987 | B2 | 6/2003 | Gellman et al. |
| 6,582,453 | B1 | 6/2003 | Tran et al. |
| 6,585,730 | B1 | 7/2003 | Foerster |
| 6,620,166 | B1 | 9/2003 | Wenstrom, Jr. et al. |
| 6,629,984 | B1 | 10/2003 | Chan |
| 6,641,596 | B1 | 11/2003 | Lizardi |
| 6,641,597 | B2 | 11/2003 | Burkhart et al. |
| 6,660,008 | B1 | 12/2003 | Foerster et al. |
| 6,660,023 | B2 | 12/2003 | McDevitt et al. |
| 6,673,094 | B1 | 1/2004 | McDevitt et al. |
| 6,692,516 | B2 | 2/2004 | West, Jr. |
| 6,733,506 | B1 | 5/2004 | McDevitt et al. |
| 6,746,457 | B2 | 6/2004 | Dana et al. |
| 6,752,814 | B2 | 6/2004 | Gellman et al. |
| 6,770,073 | B2 | 8/2004 | McDevitt et al. |
| 6,770,076 | B2 | 8/2004 | Foerster |
| 6,780,198 | B1 | 8/2004 | Gregoire et al. |
| 6,814,741 | B2 | 11/2004 | Bowman et al. |
| 6,855,157 | B2 | 2/2005 | Foerster et al. |
| 6,887,259 | B2 | 5/2005 | Lizardi |
| 6,932,834 | B2 | 8/2005 | Lizardi et al. |
| 6,942,666 | B2 | 9/2005 | Overaker et al. |
| 6,986,781 | B2 | 1/2006 | Smith |
| 6,991,636 | B2 | 1/2006 | Rose |
| 7,033,380 | B2 | 4/2006 | Schwartz et al. |
| 7,037,324 | B2 | 5/2006 | Martinek |
| 7,041,120 | B2 | 5/2006 | Li et al. |
| 7,048,755 | B2 | 5/2006 | Bonutti et al. |
| 7,074,203 | B1 | 7/2006 | Johanson et al. |
| 7,081,126 | B2 | 7/2006 | McDevitt et al. |
| 7,083,638 | B2 | 8/2006 | Foerster |
| 7,090,690 | B2 | 8/2006 | Foerster et al. |
| 7,144,415 | B2 | 12/2006 | Del Rio et al. |
| 7,160,314 | B2 | 1/2007 | Sgro et al. |
| 7,226,469 | B2 | 6/2007 | Benavitz et al. |
| 7,235,100 | B2 | 6/2007 | Martinek |
| 7,309,346 | B2 | 12/2007 | Martinek |
| 7,329,272 | B2 | 2/2008 | Burkhart et al. |
| 7,381,213 | B2 | 6/2008 | Lizardi |
| 7,507,200 | B2 | 3/2009 | Okada |
| 7,517,357 | B2 | 4/2009 | Abrams et al. |
| 7,556,640 | B2 | 7/2009 | Foerster |
| 7,637,926 | B2 | 12/2009 | Foerster et al. |
| 7,662,171 | B2 | 2/2010 | West, Jr. et al. |
| 7,674,274 | B2 | 3/2010 | Foerster et al. |
| 7,674,276 | B2 | 3/2010 | Stone et al. |
| 7,682,374 | B2 | 3/2010 | Foerster et al. |
| 7,695,494 | B2 | 4/2010 | Foerster |
| 7,704,262 | B2 | 4/2010 | Bellafiore et al. |
| 7,713,286 | B2 | 5/2010 | Singhatat |
| 7,780,701 | B1 | 8/2010 | Meridew et al. |
| 7,794,484 | B2 | 9/2010 | Stone et al. |
| 7,828,820 | B2 | 11/2010 | Stone et al. |
| 7,837,710 | B2 | 11/2010 | Lombardo et al. |
| 7,842,050 | B2 | 11/2010 | Diduch et al. |
| 7,846,167 | B2 | 12/2010 | Garcia et al. |
| 7,867,264 | B2 | 1/2011 | McDevitt et al. |
| 7,896,907 | B2 | 3/2011 | McDevitt et al. |
| 7,938,847 | B2 | 5/2011 | Fanton et al. |
| 7,963,972 | B2 | 6/2011 | Foerster et al. |
| 7,976,565 | B1 | 7/2011 | Meridew et al. |
| 7,993,369 | B2 | 8/2011 | Dreyfuss |
| 8,029,537 | B2 | 10/2011 | West, Jr. et al. |
| 8,057,524 | B2 | 11/2011 | Meridew |
| 8,066,718 | B2 | 11/2011 | Weisel et al. |
| 8,075,572 | B2 | 12/2011 | Stefanchik et al. |
| RE43,143 | E | 1/2012 | Hayhurst |
| 8,100,942 | B1 | 1/2012 | Green et al. |
| 8,109,969 | B1 | 2/2012 | Green et al. |
| 8,118,835 | B2 | 2/2012 | Weisel et al. |
| 8,128,641 | B2 | 3/2012 | Wardle |
| 8,133,258 | B2 | 3/2012 | Foerster et al. |
| 8,137,381 | B2 | 3/2012 | Foerster et al. |
| 8,137,383 | B2 | 3/2012 | West, Jr. et al. |
| 8,162,978 | B2 | 4/2012 | Lombardo et al. |
| 8,298,291 | B2 | 10/2012 | Ewers et al. |
| 8,409,252 | B2 | 4/2013 | Lombardo et al. |
| 8,435,264 | B2 | 5/2013 | Sojka et al. |
| 8,444,672 | B2 | 5/2013 | Foerster |
| 8,444,674 | B2 | 5/2013 | Kaplan |
| 8,454,704 | B2 | 6/2013 | Frushell et al. |
| 8,460,340 | B2 | 6/2013 | Soika et al. |
| 8,469,998 | B2 | 6/2013 | Sojka et al. |
| 8,491,600 | B2 | 7/2013 | McDevitt et al. |
| 8,523,902 | B2 | 9/2013 | Heaven et al. |
| 8,545,535 | B2 | 10/2013 | Hirotsuka et al. |
| 8,545,536 | B2 | 10/2013 | Mayer et al. |
| 8,613,756 | B2 | 12/2013 | Lizardi et al. |
| 8,632,568 | B2 | 1/2014 | Miller et al. |
| 8,834,543 | B2 | 9/2014 | McDevitt et al. |
| 8,986,345 | B2 | 3/2015 | Denham et al. |
| 2001/0002436 | A1 | 5/2001 | Bowman et al. |
| 2001/0049529 | A1 | 12/2001 | Cachia et al. |
| 2002/0040241 | A1 | 4/2002 | Jarvinen |
| 2002/0115999 | A1 | 8/2002 | McDevitt et al. |
| 2002/0147456 | A1 | 10/2002 | Diduch et al. |
| 2003/0004545 | A1 | 1/2003 | Burkhart et al. |
| 2003/0065361 | A1 | 4/2003 | Dreyfuss |
| 2003/0139752 | A1 | 7/2003 | Pasricha et al. |
| 2003/0195563 | A1 | 10/2003 | Foerster |
| 2003/0195564 | A1 | 10/2003 | Tran et al. |
| 2004/0093031 | A1 | 5/2004 | Burkhart et al. |
| 2004/0138706 | A1 | 7/2004 | Abrams et al. |
| 2004/0220573 | A1 | 11/2004 | McDevitt et al. |
| 2004/0249393 | A1 | 12/2004 | Weisel et al. |
| 2005/0004644 | A1 | 1/2005 | Kelsch et al. |
| 2005/0049592 | A1 | 3/2005 | Keith et al. |
| 2005/0075668 | A1 | 4/2005 | Lizardi |
| 2005/0149122 | A1 | 7/2005 | McDevitt et al. |
| 2005/0245932 | A1 | 11/2005 | Fanton et al. |
| 2005/0277986 | A1 | 12/2005 | Foerster et al. |
| 2005/0283171 | A1 | 12/2005 | Bellafiore et al. |
| 2006/0052788 | A1 | 3/2006 | Thelen et al. |
| 2006/0079904 | A1 | 4/2006 | Thal |
| 2006/0081553 | A1 | 4/2006 | Patterson et al. |
| 2006/0106423 | A1 | 5/2006 | Weisel et al. |
| 2006/0217762 | A1 | 9/2006 | Maahs et al. |
| 2006/0235413 | A1 | 10/2006 | Denham et al. |
| 2006/0265010 | A1 | 11/2006 | Paraschec et al. |
| 2006/0282081 | A1 | 12/2006 | Fanton et al. |
| 2006/0282082 | A1 | 12/2006 | Fanton et al. |
| 2006/0282083 | A1 | 12/2006 | Fanton et al. |
| 2007/0005068 | A1 | 1/2007 | Sklar |
| 2007/0060922 | A1 | 3/2007 | Dreyfuss |
| 2007/0093858 | A1 | 4/2007 | Gambale et al. |
| 2007/0142835 | A1 | 6/2007 | Green et al. |
| 2007/0156149 | A1 | 7/2007 | Fanton et al. |
| 2007/0156150 | A1 | 7/2007 | Fanton et al. |
| 2007/0156176 | A1 | 7/2007 | Fanton et al. |
| 2007/0203498 | A1 | 8/2007 | Gerber et al. |

(56) References Cited

U.S. PATENT DOCUMENTS

2007/0219557 A1 9/2007 Bourque et al.
2007/0255317 A1 11/2007 Fanton et al.
2007/0260259 A1 11/2007 Fanton et al.
2007/0270889 A1 11/2007 Conlon et al.
2007/0270907 A1 11/2007 Stokes et al.
2007/0288027 A1 12/2007 Grafton et al.
2008/0033460 A1 2/2008 Ziniti et al.
2008/0086138 A1 4/2008 Stone et al.
2008/0275469 A1 11/2008 Fanton et al.
2008/0294177 A1 11/2008 To et al.
2008/0306510 A1 12/2008 Stchur
2009/0018554 A1 1/2009 Thorne et al.
2009/0082807 A1 3/2009 Miller et al.
2009/0099598 A1 4/2009 McDevitt et al.
2009/0112214 A1 4/2009 Philippon et al.
2009/0192545 A1 7/2009 Workman
2009/0222041 A1 9/2009 Foerster
2009/0248068 A1 10/2009 Lombardo et al.
2009/0292321 A1 11/2009 Collette
2009/0299386 A1 12/2009 Meridew
2009/0306711 A1 12/2009 Stone et al.
2009/0312794 A1 12/2009 Nason et al.
2010/0004683 A1 1/2010 Hoof et al.
2010/0049213 A1 2/2010 Serina et al.
2010/0063542 A1 3/2010 van der Burg et al.
2010/0069925 A1 3/2010 Friedman et al.
2010/0094314 A1 4/2010 Hernlund et al.
2010/0094355 A1 4/2010 Trenhaile
2010/0094425 A1 4/2010 Bentley et al.
2010/0100127 A1 4/2010 Trenhaile
2010/0114162 A1 5/2010 Bojarski et al.
2010/0121348 A1 5/2010 van der Burg et al.
2010/0121349 A1 5/2010 Meier et al.
2010/0191283 A1 7/2010 Foerster et al.
2010/0198258 A1 8/2010 Heaven et al.
2010/0222812 A1 9/2010 Stone et al.
2010/0251861 A1 10/2010 Sixto, Jr. et al.
2010/0292731 A1 11/2010 Gittings et al.
2010/0305576 A1 12/2010 Ferguson et al.
2011/0015674 A1 1/2011 Howard et al.
2011/0046682 A1 2/2011 Stephan et al.
2011/0071545 A1 3/2011 Pamichev et al.
2011/0071549 A1 3/2011 Caborn et al.
2011/0098728 A1 4/2011 McDevitt et al.
2011/0152929 A1 6/2011 McDevitt et al.
2011/0224726 A1 9/2011 Lombardo et al.
2011/0238113 A1 9/2011 Fanton et al.
2011/0264140 A1 10/2011 Lizardi et al.
2011/0295279 A1 12/2011 Stone et al.
2011/0301621 A1 12/2011 Oren et al.
2011/0301622 A1 12/2011 Oren et al.
2012/0041485 A1 2/2012 Kaiser et al.
2012/0053629 A1 3/2012 Reiser et al.
2012/0059417 A1 3/2012 Norton et al.
2012/0143221 A1 6/2012 Weisel et al.
2012/0150223 A1 6/2012 Manos et al.
2013/0006276 A1 1/2013 Lantz et al.
2013/0023930 A1 1/2013 Stone et al.
2013/0096611 A1 4/2013 Sullivan
2013/0103083 A1 4/2013 Baird
2013/0138152 A1 5/2013 Stone et al.
2013/0144334 A1 6/2013 Bouduban et al.
2013/0144338 A1 6/2013 Stone et al.
2013/0184748 A1 7/2013 Sojka et al.
2013/0204298 A1 8/2013 Graul et al.
2013/0267998 A1 10/2013 Vijay et al.
2013/0296931 A1 11/2013 Sengun
2014/0249579 A1 9/2014 Heaven et al.
2014/0257382 A1 9/2014 McCartney
2014/0316460 A1 10/2014 Graul et al.
2015/0100087 A1 4/2015 Graul et al.

FOREIGN PATENT DOCUMENTS

EP 0 251 583 1/1988
EP 0 270 704 6/1988
EP 0 318 426 5/1989
EP 0 574 707 12/1993
EP 0 673 624 9/1995
EP 0 834 281 4/1998
EP 1 016 377 7/2000
EP 1 568 327 8/2005
EP 1 762 187 3/2007
EP 1 825 817 8/2007
EP 2 335 603 6/2011
WO WO 92/04874 4/1992
WO WO 95/15726 6/1995
WO WO 97/03615 2/1997
WO WO 97/30649 8/1997
WO WO 98/38938 9/1998
WO WO 2008/063915 5/2008
WO WO 2011/060022 5/2011
WO WO 2012/034131 3/2012

HIP JOINT

CAM-TYPE FEMOROACETABULAR IMPINGEMENT (FAI)

CAM INJURY TO THE LABRUM

PINCER-TYPE FEMOROACETABULAR IMPINGEMENT (FAI)

PINCER INJURY TO THE LABRUM

ANCHOR WITH DEPLOYMENT CYLINDER

CROWN FEATURE FLEXES TO FIT IN DELIVERY TUBE AND EXPANDS IN AN ELASTIC MANNER TO A DIAMETER LARGER THAN THE DELIVERY TUBE WHEN INSERTED INTO BONE

CAPTURE COUPLING FOR INSERTION

T-NOTCH COUPLING FOR INSERTION

BALL AND SOCKET COUPLING FOR INSERTION (ESPECIALLY HELPS WITH CURVED SYSTEM)

85
75
10

SLIT THROUGH
ONE SIDE
PLUS MATERIAL
BARB
85
75
10

SLIT THROUGH
BOTH SIDES
PLUS MATERIAL
BARB
85
75
10

SLIT THROUGH BOTH
SIDES
MINUS MATERIAL
BARB

NON-CONCENTRIC THROUGH HOLE

NO SLIT
PLUS MATERIAL
BARB

METHOD AND APPARATUS FOR RE-ATTACHING THE LABRUM TO THE ACETABULUM, INCLUDING THE PROVISION AND USE OF A NOVEL SUTURE ANCHOR SYSTEM

REFERENCE TO PENDING PRIOR PATENT APPLICATIONS

This patent application is a continuation of pending prior U.S. patent application Ser. No. 13/642,168, filed Dec. 26, 2012 by Chris Pamichev et al. for METHOD AND APPARATUS FOR RE-ATTACHING THE LABRUM TO THE ACETABULUM, INCLUDING THE PROVISION AND USE OF A NOVEL SUTURE ANCHOR SYSTEM, which in turn is a 371 national stage entry of International (PCT) Patent Application No. PCT/US11/21173, filed Jan. 13, 2011 by Pivot Medical, Inc. for METHOD AND APPARATUS FOR RE-ATTACHING THE LABRUM TO THE ACETABULUM, INCLUDING THE PROVISION AND USE OF A NOVEL SUTURE ANCHOR SYSTEM, which in turn:

(i) is a continuation-in-part of prior U.S. patent application Ser. No. 12/839,246, filed Jul. 19, 2010 by Chris Pamichev et al. for METHOD AND APPARATUS FOR RE-ATTACHING THE LABRUM TO THE ACETABULUM, INCLUDING THE PROVISION AND USE OF A NOVEL SUTURE ANCHOR SYSTEM, which in turn claims benefit of (1) prior U.S. Provisional Patent Application Ser. No. 61/271,205, filed Jul. 17, 2009 by Chris Pamichev et al. for METHOD AND APPARATUS FOR RE-SECURING THE LABRUM TO THE ACETABULUM, INCLUDING THE PROVISION AND USE OF A NOVEL NANO TACK SYSTEM, and (2) prior U.S. Provisional Patent Application Ser. No. 61/326,709, filed Apr. 22, 2010 by Chris Pamichev et al. for METHOD AND APPARATUS FOR RE-SECURING THE LABRUM TO THE ACETABULUM, INCLUDING THE PROVISION AND USE OF A NOVEL SUTURE ANCHOR SYSTEM; and (ii) claims benefit of prior U.S. Provisional Patent Application Ser. No. 61/326,709, filed Apr. 22, 2010 by Chris Pamichev et al. for METHOD AND APPARATUS FOR RE-SECURING THE LABRUM TO THE ACETABULUM, INCLUDING THE PROVISION AND USE OF A NOVEL SUTURE ANCHOR SYSTEM.

The above-identified patent applications are hereby incorporated herein by reference.

FIELD OF THE INVENTION

This invention relates to surgical methods and apparatus in general, and more particularly to surgical methods and apparatus for treating a hip joint.

BACKGROUND OF THE INVENTION

The Hip Joint in General

The hip joint is a ball-and-socket joint which movably connects the leg to the torso. The hip joint is capable of a wide range of different motions, e.g., flexion and extension, abduction and adduction, medial and lateral rotation, etc. See FIGS. 1A, 1B, 1C and 1D.

With the possible exception of the shoulder joint, the hip joint is perhaps the most mobile joint in the body. Significantly, and unlike the shoulder joint, the hip joint carries substantial weight loads during most of the day, in both static (e.g., standing and sitting) and dynamic (e.g., walking and running) conditions.

The hip joint is susceptible to a number of different pathologies. These pathologies can have both congenital and injury-related origins. In some cases, the pathology can be substantial at the outset. In other cases, the pathology may be minor at the outset but, if left untreated, may worsen over time. More particularly, in many cases, an existing pathology may be exacerbated by the dynamic nature of the hip joint and the substantial weight loads imposed on the hip joint.

The pathology may, either initially or thereafter, significantly interfere with patient comfort and lifestyle. In some cases, the pathology can be so severe as to require partial or total hip replacement. A number of procedures have been developed for treating hip pathologies short of partial or total hip replacement, but these procedures are generally limited in scope due to the significant difficulties associated with treating the hip joint.

A better understanding of various hip joint pathologies, and also the current limitations associated with their treatment, can be gained from a more thorough understanding of the anatomy of the hip joint.

Anatomy of the Hip Joint

The hip joint is formed at the junction of the leg and the torso. More particularly, and looking now at FIG. 2, the head of the femur is received in the acetabular cup of the hip, with a plurality of ligaments and other soft tissue serving to hold the bones in articulating condition.

More particularly, and looking now at FIG. 3, the femur is generally characterized by an elongated body terminating, at its top end, in an angled neck which supports a hemispherical head (also sometimes referred to as "the ball"). As seen in FIGS. 3 and 4, a large projection known as the greater trochanter protrudes laterally and posteriorly from the elongated body adjacent to the neck of the femur. A second, somewhat smaller projection known as the lesser trochanter protrudes medially and posteriorly from the elongated body adjacent to the neck. An intertrochanteric crest (FIGS. 3 and 4) extends along the periphery of the femur, between the greater trochanter and the lesser trochanter.

Looking next at FIG. 5, the hip socket is made up of three constituent bones: the ilium, the ischium and the pubis. These three bones cooperate with one another (they typically ossify into a single "hip bone" structure by the age of 25 or so) in order to collectively form the acetabular cup. The acetabular cup receives the head of the femur.

Both the head of the femur and the acetabular cup are covered with a layer of articular cartilage which protects the underlying bone and facilitates motion. See FIG. 6.

Various ligaments and soft tissue serve to hold the ball of the femur in place within the acetabular cup. More particularly, and looking now at FIGS. 7 and 8, the ligamentum teres extends between the ball of the femur and the base of the acetabular cup. As seen in FIGS. 8 and 9, a labrum is disposed about the perimeter of the acetabular cup. The labrum serves to increase the depth of the acetabular cup and effectively establishes a suction seal between the ball of the femur and the rim of the acetabular cup, thereby helping to hold the head of the femur in the acetabular cup. In addition to the foregoing, and looking now at FIG. 10, a fibrous capsule extends between the neck of the femur and the rim of the acetabular cup, effectively sealing off the ball-and-socket members of the hip joint from the remainder of the body. The foregoing structures (i.e., the ligamentum teres, the labrum and the fibrous capsule) are encompassed and reinforced by a set of three main ligaments (i.e., the iliofemoral ligament, the ischiofemoral ligament and the pubofemoral ligament) which extend between the femur and the perimeter of the hip socket. See, for example, FIGS. 11 and 12, which show the iliofemoral ligament, with FIG. 11 being an anterior view and FIG. 12 being a posterior view.

Pathologies of the Hip Joint

As noted above, the hip joint is susceptible to a number of different pathologies. These pathologies can have both congenital and injury-related origins.

By way of example but not limitation, one important type of congenital pathology of the hip joint involves impingement between the neck of the femur and the rim of the acetabular cup. In some cases, and looking now at FIG. 13, this impingement can occur due to irregularities in the geometry of the femur. This type of impingement is sometimes referred to as cam-type femoroacetabular impingement (i.e., cam-type FAI). In other cases, and looking now at FIG. 14, the impingement can occur due to irregularities in the geometry of the acetabular cup. This latter type of impingement is sometimes referred to as pincer-type femoroacetabular impingement (i.e., pincer-type FAI). Impingement can result in a reduced range of motion, substantial pain and, in some cases, significant deterioration of the hip joint.

By way of further example but not limitation, another important type of congenital pathology of the hip joint involves defects in the articular surface of the ball and/or the articular surface of the acetabular cup. Defects of this type sometimes start out fairly small but often increase in size over time, generally due to the dynamic nature of the hip joint and also due to the weight-bearing nature of the hip joint. Articular defects can result in substantial pain, induce and/or exacerbate arthritic conditions and, in some cases, cause significant deterioration of the hip joint.

By way of further example but not limitation, one important type of injury-related pathology of the hip joint involves trauma to the labrum. More particularly, in many cases, an accident or sports-related injury can result in the labrum being torn away from the rim of the acetabular cup, typically with a tear running through the body of the labrum. See FIG. 15. These types of injuries can be very painful for the patient and, if left untreated, can lead to substantial deterioration of the hip joint.

The General Trend Toward Treating Joint Pathologies Using Minimally-Invasive, and Earlier, Interventions The current trend in orthopedic surgery is to treat joint pathologies using minimally-invasive techniques. Such minimally-invasive, "keyhole" surgeries generally offer numerous advantages over traditional, "open" surgeries, including reduced trauma to tissue, less pain for the patient, faster recuperation times, etc.

By way of example but not limitation, it is common to re-attach ligaments in the shoulder joint using minimally-invasive, "keyhole" techniques which do not require large incisions into the interior of the shoulder joint. By way of further example but not limitation, it is common to repair torn meniscal cartilage in the knee joint, and/or to replace ruptured ACL ligaments in the knee joint, using minimally-invasive techniques.

While such minimally-invasive approaches can require additional training on the part of the surgeon, such procedures generally offer substantial advantages for the patient and have now become the standard of care for many shoulder joint and knee joint pathologies.

In addition to the foregoing, in view of the inherent advantages and widespread availability of minimally-invasive approaches for treating pathologies of the shoulder joint and knee joint, the current trend is to provide such treatment much earlier in the lifecycle of the pathology, so as to address patient pain as soon as possible and so as to minimize any exacerbation of the pathology itself. This is in marked contrast to traditional surgical practices, which have generally dictated postponing surgical procedures as long as possible so as to spare the patient from the substantial trauma generally associated with invasive surgery.

Treatment for Pathologies of the Hip Joint

Unfortunately, minimally-invasive treatments for pathologies of the hip joint have lagged far behind minimally-invasive treatments for pathologies of the shoulder joint and the knee joint. This is generally due to (i) the constrained geometry of the hip joint itself, and (ii) the nature and location of the pathologies which must typically be addressed in the hip joint.

More particularly, the hip joint is generally considered to be a "tight" joint, in the sense that there is relatively little room to maneuver within the confines of the joint itself. This is in marked contrast to the shoulder joint and the knee joint, which are generally considered to be relatively "spacious" joints (at least when compared to the hip joint). As a result, it is relatively difficult for surgeons to perform minimally-invasive procedures on the hip joint.

Furthermore, the pathways for entering the interior of the hip joint (i.e., the natural pathways which exist between adjacent bones and/or delicate neurovascular structures) are generally much more constraining for the hip joint than for the shoulder joint or the knee joint. This limited access further complicates effectively performing minimally-invasive procedures on the hip joint.

In addition to the foregoing, the nature and location of the pathologies of the hip joint also complicate performing minimally-invasive procedures on the hip joint. By way of example but not limitation, consider a typical detachment of the labrum in the hip joint. In this situation, instruments must generally be introduced into the joint space using an angle of approach which is offset from the angle at which the instrument addresses the tissue. This makes drilling into bone, for example, significantly more complicated than where the angle of approach is effectively aligned with the angle at which the instrument addresses the tissue, such as is frequently the case in the shoulder joint. Furthermore, the working space within the hip joint is typically extremely limited, further complicating repairs where the angle of approach is not aligned with the angle at which the instrument addresses the tissue.

As a result of the foregoing, minimally-invasive hip joint procedures are still relatively difficult to perform and relatively uncommon in practice. Consequently, patients are typically forced to manage their hip pain for as long as possible, until a resurfacing procedure or a partial or total hip replacement procedure can no longer be avoided. These procedures are generally then performed as a highly-invasive, open procedure, with all of the disadvantages associated with highly-invasive, open procedures.

As a result, there is, in general, a pressing need for improved methods and apparatus for treating pathologies of the hip joint.

Re-Attaching the Labrum of the Hip Joint

As noted above, hip arthroscopy is becoming increasingly more common in the diagnosis and treatment of various hip pathologies. However, due to the anatomy of the hip joint and the pathologies associated with the same, hip arthroscopy is currently practical for only selected pathologies and, even then, hip arthroscopy has generally met with limited success.

One procedure which is sometimes attempted arthroscopically relates to the repair of a torn and/or detached labrum. This procedure may be attempted (i) when the labrum has been damaged but is still sufficiently healthy and intact as to be capable of repair and/or re-attachment, and (ii) when the labrum has been deliberately detached (e.g., so as to allow for acetabular rim trimming to treat a pathology such as a pincer-type FAI) and needs to be subsequently re-attached. See, for example, FIG. 16, which shows a normal labrum which has its base securely attached to the acetabulum, and FIG. 17, which shows a portion of the labrum (in this case the tip) detached from the acetabulum. In this respect it should also be appreciated that repairing the labrum rather than removing the labrum is generally desirable, inasmuch as studies have shown that patients whose labrum has been repaired tend to have better long-term outcomes than patients whose labrum has been removed.

Unfortunately, current methods and apparatus for arthroscopically repairing (e.g., re-attaching) the labrum are somewhat problematic. The present invention is intended to improve upon the current approaches for labrum repair.

More particularly, current approaches for arthroscopically repairing the labrum typically use apparatus originally designed for use in re-attaching ligaments to bone. For example, one such approach utilizes a screw-type bone anchor, with two sutures extending therefrom, and involves deploying the bone anchor in the acetabulum above the labrum re-attachment site. A first one of the sutures is passed either through the detached labrum or, alternatively, around the detached labrum. Then the first suture is tied to the second suture so as to support the labrum against the acetabular rim. See FIG. 18.

Unfortunately, bone anchors of the sort described above are traditionally used for re-attaching ligaments to bone and, as a result, tend to be relatively large, since they must carry the substantial pull-out forces normally associated with ligament reconstruction. However, this large anchor size is generally unnecessary for labrum re-attachment, since the labrum is not subjected to substantial pull-out forces, and the large anchor size typically causes unnecessary trauma to the patient.

Furthermore, the large size of traditional bone anchors can be problematic when the anchors are used for labrum re-attachment, since the bone anchors generally require a substantial bone mass for secure anchoring, and such a large bone mass is generally available only a substantial distance up the acetabular shelf. In addition, the large size of the bone anchors generally makes it necessary to set the bone anchor a substantial distance up the acetabular shelf, in order to ensure that the distal tip of the bone anchor does not inadvertently break through the acetabular shelf and contact the articulating surfaces of the joint. However, labral re-attachment utilizing a bone anchor set high up into the acetabular shelf creates a suture path, and hence a labral draw force, which is not directly aligned with the portion of the acetabular rim where the labrum is to be re-attached. As a result, an "indirect" draw force (also known as eversion) is typically applied to the labrum, i.e., the labrum is drawn around the rim of the acetabulum rather than directly into the acetabulum. See FIG. 18. This can sometimes result in a problematic labral re-attachment and, ultimately, can lead to a loss of the suction seal between the labrum and femoral head, which is a desired outcome of the labral re-attachment procedure.

Alternatively, the suture path can also surround the labrum, thus placing a suture on both sides of the labrum, including the articular side of the labrum, and thus exposing the articular surface of the femur to a foreign body, which could in turn cause damage to the articular surface (i.e., the articular cartilage) of the femur.

Accordingly, a new approach is needed for arthroscopically re-attaching the labrum to the acetabulum.

SUMMARY OF THE INVENTION

The present invention provides a novel method and apparatus for re-attaching the labrum to the acetabulum. Among other things, the present invention comprises the provision and use of a novel suture anchor system.

In one form of the invention, there is provided apparatus for securing a first object to a second object, the apparatus comprising:

an elongated body having a distal end, a proximal end, and a lumen extending between the distal end and the proximal end, the lumen comprising a first section and a second section, the first section of the lumen being disposed distal to the second section of the lumen, and with the first section of the lumen having a wider diameter than the second section of the lumen;

at least one longitudinally-extending slit extending through the side wall of the elongated body and communicating with the lumen, the at least one longitudinally-extending slit having a distal end and a proximal end, with the distal end of the at least one longitudinally-extending slit being spaced from the distal end of the elongated body; and an elongated element extending through the lumen of the elongated body, the elongated element comprising a proximal end and a distal end and having an enlargement at its distal end, the enlargement having a diameter greater than the second section of the lumen.

In another form of the invention, there is provided apparatus for securing a first object to a second object, the apparatus comprising:

an elongated body having a distal end, a proximal end, and a lumen extending between the distal end and the proximal end, the lumen comprising a first section and a second section, the first section of the lumen being disposed distal to the second section of the lumen, and with the first section of the lumen having a wider diameter than the second section of the lumen; and a suture extending through the lumen of the elongated body, the suture comprising a proximal end and a distal end and having a suture knot at its distal end, the suture knot having a diameter greater than the second section of the lumen.

In another form of the invention, there is provided apparatus for securing a first object to a second object, the apparatus comprising:

an elongated body having a distal end, a proximal end, and a lumen extending between the distal end and the proximal end, the lumen comprising a first section and a second section, the first section of the lumen being disposed distal to the second section of the lumen and with the first section of the lumen having a wider diameter than the second section of the lumen;

the side wall of the elongated body having a weakened section therein adjacent to the second section of the lumen; and an elongated element extending through the lumen of the elongated body, the elongated element comprising a proximal end and a distal end and having an enlargement at its distal end, the enlargement having a diameter greater than the second section of the lumen.

In another form of the invention, there is provided a method for securing a first object to a second object, the method comprising:

providing apparatus comprising:

an elongated body having a distal end, a proximal end, and a lumen extending between the distal end and the proximal end, the lumen comprising a first section and a second section, the first section of the lumen being disposed distal to the second section of the lumen, and with the first section of the lumen having a wider diameter than the second section of the lumen;

at least one longitudinally-extending slit extending through the side wall of the elongated body and communicating with the lumen, the at least one longitudinally-extending slit having a distal end and a proximal end, with the distal end of the at least one longitudinally-extending slit being spaced from the distal end of the elongated body; and an elongated element extending through the lumen of the elongated body, the elongated element comprising a proximal end and a distal end and having an enlargement at its distal end, the enlargement having a diameter greater than the second section of the lumen;

inserting the elongated body into the second object;

moving the enlargement proximally so as to expand the elongated body; and securing the first object to the second object with the elongated element.

In another form of the invention, there is provided a method for securing a first object to a second object, the method comprising:

providing apparatus comprising:

an elongated body having a distal end, a proximal end, and a lumen extending between the distal end and the proximal end, the lumen comprising a first section and a second section, the first section of the lumen being disposed distal to the second section of the lumen, and with the first section of the lumen having a wider diameter than the second section of the lumen; and a suture extending through the lumen of the elongated body, the suture comprising a proximal end and a distal end and having a suture knot at its distal end, the suture knot having a diameter greater than the second section of the lumen;

inserting the elongated body into the second object;

moving the suture knot proximally so as to expand the elongated body; and securing the first object to the second object with the suture.

In another form of the invention, there is provided a method for securing a first object to a second object, the method comprising:

providing apparatus comprising:

an elongated body having a distal end, a proximal end, and a lumen extending between the distal end and the proximal end, the lumen comprising a first section and a second section, the first section of the lumen being disposed distal to the second section of the lumen, and with the first section of the lumen having a wider diameter than the second section of the lumen;

the side wall of the elongated body having a weakened section therein adjacent to the second section of the lumen; and an elongated element extending through the lumen of the elongated body, the elongated element comprising a proximal end and a distal end and having an enlargement at its distal end, the enlargement having a diameter greater than the second section of the lumen;

inserting the elongated body into the second object;

moving the enlargement proximally so as to expand the elongated body; and securing the first object to the second object with the elongated element.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE INVENTION

The Novel Suture Anchor System of the Present Invention in General

The present invention provides a novel method and apparatus for arthroscopically re-attaching the labrum to the acetabulum. Among other things, the present invention comprises the provision and use of a novel suture anchor system.

Figure 19:
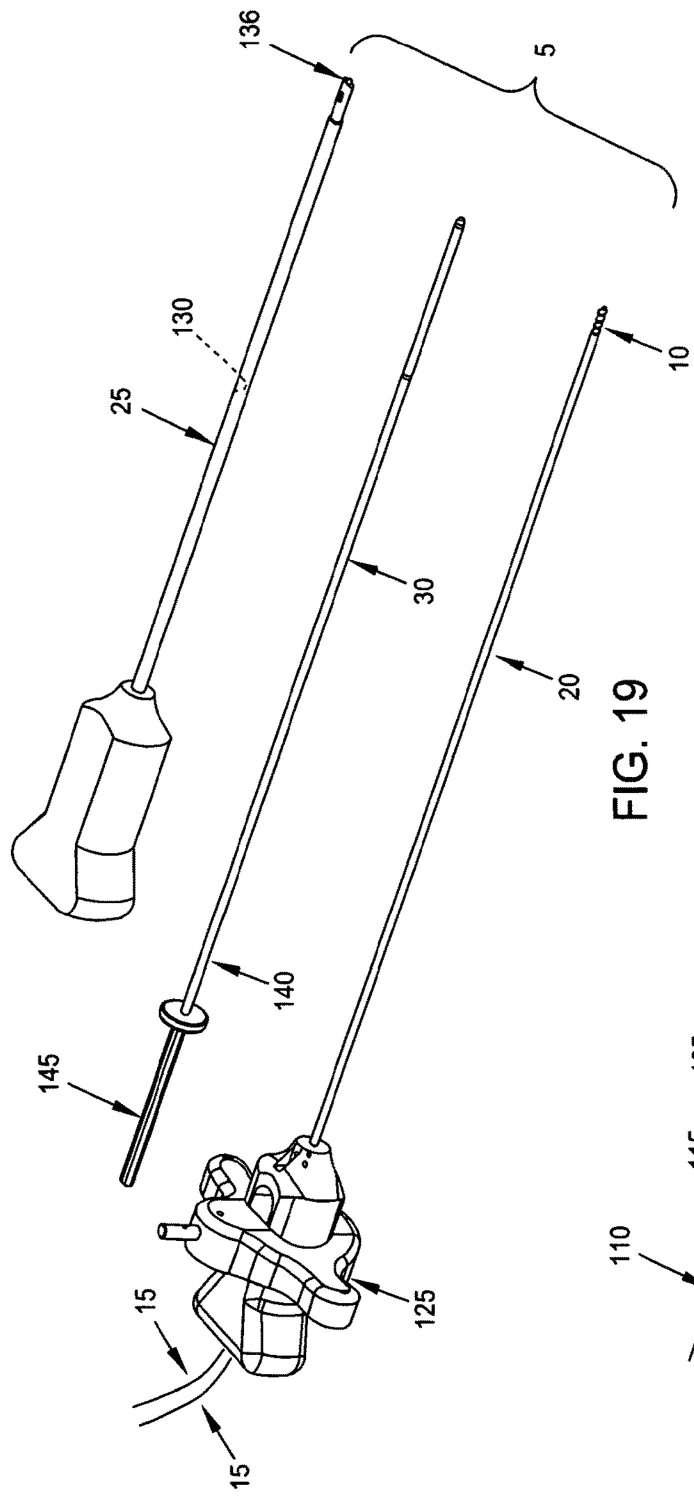
FIGS. 19-27 are schematic views showing a novel suture anchor system for use in arthroscopically re-attaching a detached labrum to the acetabulum.

More particularly, and looking now at FIG. 19, there is shown a novel suture anchor system 5 for use in arthroscopically re-attaching a detached labrum to the acetabulum. Suture anchor system 5 generally comprises an anchor 10, a suture 15 secured to anchor 10, and an inserter 20 for delivering anchor 10 into the acetabulum, whereby suture 15 may be used to secure a detached labrum to the acetabular rim as will hereinafter be discussed in further detail. Suture anchor system 5 preferably also comprises a hollow guide 25 for delivering components from outside of the body to the acetabulum, and a punch (or drill) 30 which may be used to prepare a seat for anchor 10 in the acetabulum.

Figures 21, 22, 23:
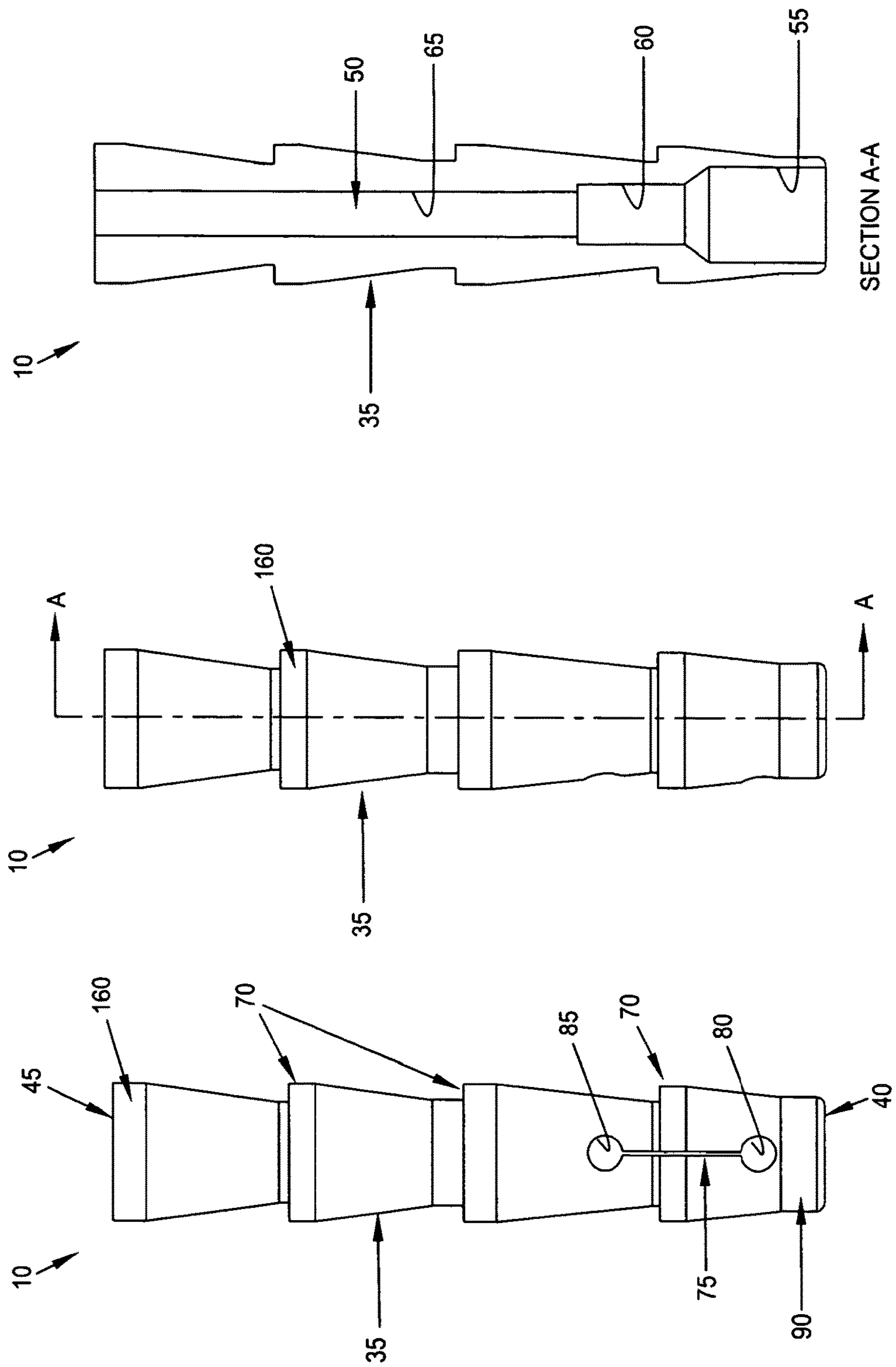
Figure 26:
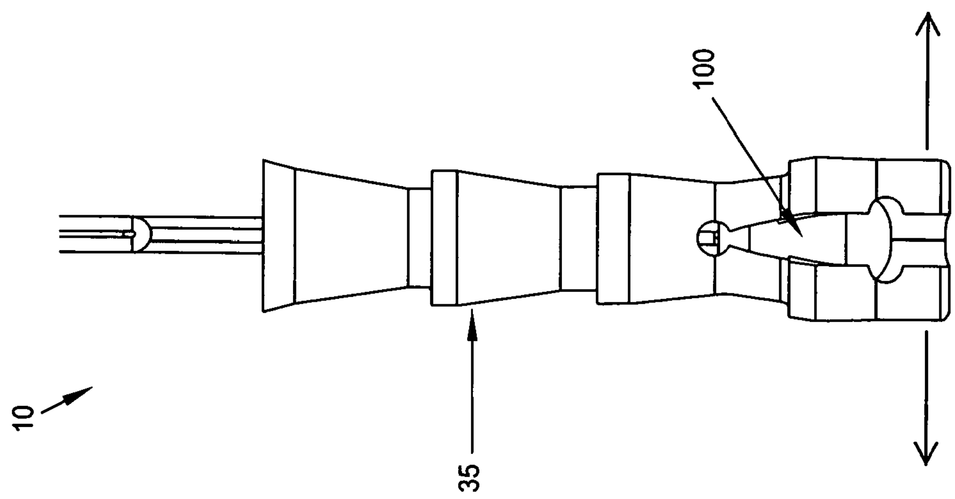
Figure 25:
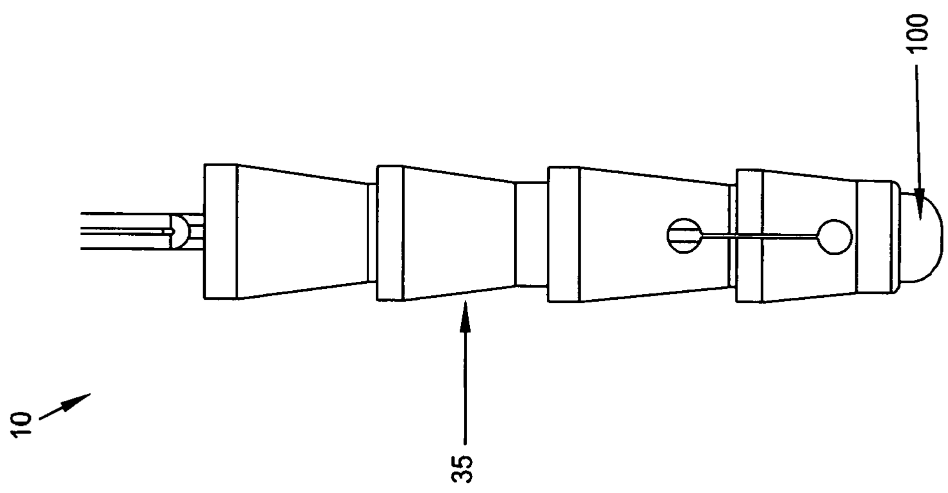
Figure 24:
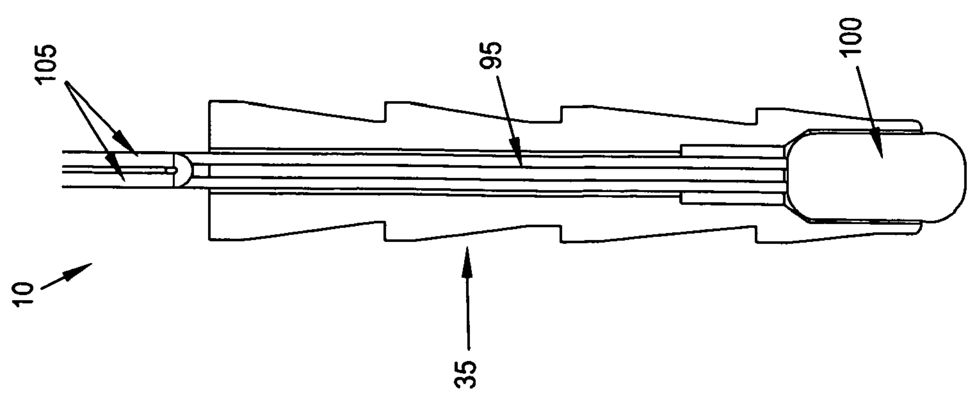

Looking next at FIGS. 19-23, anchor 10 comprises a generally cylindrical body 35 having a distal end 40, a proximal end 45, and a lumen 50 extending between distal end 40 and proximal end 45. In one preferred form of the present invention, lumen 50 comprises a distal end reservoir 55, a short intermediate portion 60, and an elongated proximal portion 65. As seen in FIG. 23, distal end reservoir 55 has a diameter which is greater than the diameter of short intermediate portion 60, and short intermediate portion 60 has a diameter which is greater than the diameter of elongated proximal portion 65. And in one preferred form of the present invention, the outer surface of generally cylindrical body 35 comprises a plurality of ribs 70 spaced along the length of generally cylindrical body 35, so as to enhance the "holding power" of anchor 10 in bone. In one particularly preferred form of the present invention, ribs 70 sub-divide the length of generally cylindrical body 35 into a plurality of segments, with each segment having a generally frusto-conical configuration (FIGS. 21 and 22).

Near (but spaced from) the distal end 40 of generally cylindrical body 35, there is provided a longitudinally-extending slit 75 which extends completely through one side wall (but not the other) of generally cylindrical body 35. Thus, longitudinally-extending slit 75 communicates with lumen 50 of anchor 10. The distal end of longitudinally-extending slit 75 terminates in a distal relief hole 80, and the proximal end of longitudinally-extending slit 75 terminates in a proximal relief hole 85. It will be appreciated that distal relief hole 80 is spaced from distal end 40 of generally cylindrical body 35, so that a solid distal ring 90 is located at the distal end of generally cylindrical body 35, whereby to provide the distal end of generally cylindrical body 35 with a degree of structural integrity.

Looking now at FIGS. 20 and 24-26, suture 15 generally comprises a distal loop 95 terminating in an enlargement 100 at its distal end and connected to a proximal open loop 105 at its proximal end. More particularly, distal loop 95 extends through short intermediate portion 60 and elongated proximal portion 65 of lumen 50. Enlargement 100 may comprise a solid member (e.g., cylindrical, conical, etc.) attached to the distal end of distal loop 95, or it may comprise a suture knot formed by knotting off the distal ends of distal loop 95 of suture 15, etc. Where enlargement 100 comprises a suture knot, this suture knot may or may not be hardened, shaped or stabilized with cement, heat, etc. For purposes of illustration, enlargement 100 is shown in the drawings schematically, i.e., as a generally cylindrical structure, but it should be appreciated that this is being done solely for clarity of illustration, and enlargement 100 may assume any other shapes and/or configurations (including that of a suture knot) consistent with the present invention. Enlargement 100 is sized so that it is small enough to be seated in distal end reservoir 55 of generally cylindrical body 35 (see, for example, FIGS. 24 and 25), but large enough so that it may not enter short intermediate portion 60 of generally cylindrical body 35 without causing radial expansion of generally cylindrical body 35 (see, for example, FIG. 26). Proximal open loop 105 extends back through the interior of inserter 20 (FIGS. 19 and 20) and provides a pair of free suture ends emanating from the proximal end of inserter 20 (FIG. 19), as will hereinafter be discussed.

Figure 20:
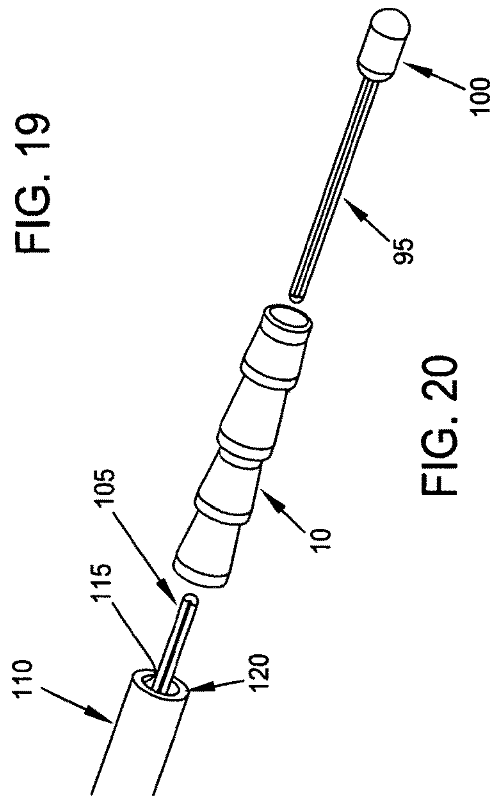

Looking now at FIGS. 19 and 20, inserter 20 generally comprises a hollow push tube 110 having a lumen 115 extending therethrough. Inserter 20 terminates at its distal end in a drive surface 120 for engaging the proximal end 45 of anchor 10, and terminates at its proximal end in a handle 125. Handle 125 may include features to secure the free ends of suture 15, e.g., one or more suture cleats, suture slots, suture clamps, etc. Where such features are provided, and where appropriate, handle 125 may also include one or more release mechanisms to release the free ends of suture 15. Handle 125 may also have one or more mechanisms to apply tension to the secured free ends of suture 15. Suture 15 (i.e., proximal open loop 105 of suture 15) extends through lumen 115 of hollow push tube 110. By maintaining a slight proximally-directed tension on the proximal end of suture 15 (e.g., by maintaining a slight proximally-directed tension on the free suture ends of proximal open loop 105), anchor 10 can be held against the drive surface 120 of hollow push tube 110, thereby providing a degree of control for maneuvering the anchor.

Preferably anchor 10, suture 15 and inserter 20 are pre-assembled into a single unit, with suture 15 extending back through lumen 115 of inserter 20 with a slight proximal tension so as to hold anchor 10 on the distal end of inserter 20.

Suture anchor system 5 preferably also comprises a hollow guide 25 for guiding components from outside of the body to the acetabulum. More particularly, hollow guide 25 generally comprises a lumen 130 for slidably receiving anchor 10 and inserter 20 therein, as will hereinafter be discussed. The internal diameter of hollow guide 25 is preferably approximately equal to the largest external feature of anchor 10 (e.g., one or more of the barbs 70), so that anchor 10 can make a close sliding fit within the interior of hollow guide 25. Alternatively, the internal diameter of hollow guide 25 may be slightly smaller or larger than the largest external feature of anchor 10 if desired. Where suture anchor system 5 also comprises a punch (or drill) 30, lumen 130 of hollow guide 25 is preferably sized to slidably receive punch (or drill) 30, as will hereinafter be discussed. The distal end of hollow guide 25 preferably includes a sharp tip/edge for penetrating the labrum and engaging the acetabulum, as will hereinafter be discussed.

Figure 27:
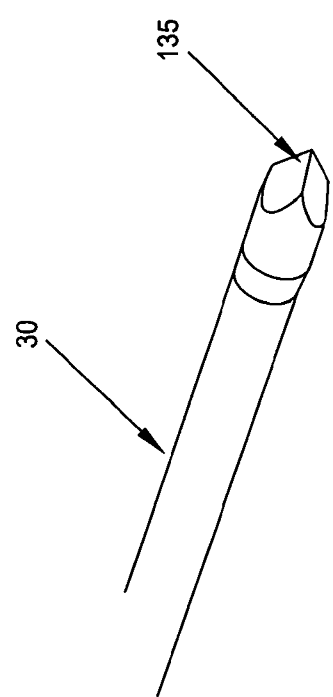

If desired, and looking now at FIGS. 19 and 27, suture anchor system 5 may also comprise a punch (or drill) 30 having a sharp distal end 135 and a proximal end 140 having a handle 145 mounted thereto. Where element 30 is a drill, handle 145 could comprise a mount for the drill so as to facilitate turning the drill with a powered driver, etc. Again, the sharp distal end 135 of punch (or drill) 30 is adapted to penetrate the acetabulum, as will hereinafter be discussed.

Method for Arthroscopically Re-Attaching the Labrum to the Acetabulum Using the Novel Suture Anchor System of the Present Invention Suture anchor system 5 is preferably used as follows to secure a detached labrum to the acetabulum.

First, the sharp distal end 136 of hollow guide 25 is passed through the labrum and positioned against the acetabulum at the location where anchor 10 is to be deployed. Preferably the sharp distal end of hollow guide 25 penetrates through the labrum and a short distance into the acetabulum so as to stabilize the hollow guide vis-à-vis the acetabulum. A stylet (e.g., an obturator) may be used to fill the hollow guide 25 during such insertion and thus prevent tissue coring of the labrum during insertion. The distal portion of the punch (or drill) 30 may also be used to fill the hollow tip of the hollow guide 25 during such insertion.

Next, if desired, punch (or drill) 30 may be used to prepare a seat in the acetabulum to receive anchor 10. More particularly, if punch (or drill) 30 is used, the sharp distal end 135 of punch (or drill) 30 is passed through hollow guide 25 (thereby also passing through the labrum) and advanced into the acetabulum so as to form an opening (i.e., a seat) in the bone to receive anchor 10. Then, while hollow guide 25 remains stationary, punch (or drill) 30 is removed from hollow guide 25.

Next, inserter 20, carrying anchor 10 thereon, is passed through hollow guide 25 (thereby also passing through the labrum) and into the seat formed in the acetabulum. As anchor 10 is advanced into the bone, the body of anchor 10 (e.g., ribs 70) makes an interference fit with the surrounding bone, whereby to initially bind the anchor to the bone. At the same time, the solid distal ring 90 located at the distal end of the anchor provides the structural integrity needed to keep the anchor intact while it penetrates into the bone. When anchor 10 has been advanced an appropriate distance into the acetabulum, the proximal end of suture 15 (i.e., proximal open loop 105) is pulled proximally while the distal end of inserter 20 is held in position, thereby causing enlargement 100 to move proximally relative to the generally cylindrical body 35, forcing the distal end of generally cylindrical body 35 to split and expand, in the manner shown in FIG. 26, whereby to further bind anchor 10, and hence suture 15, to the bone. In one preferred form of the present invention, expansion of generally cylindrical body 35 occurs along some or all of the circumference of the generally cylindrical body, and there may be variations in the amount of expansion about the circumference of the generally cylindrical body, e.g., with the construction shown in FIG. 26, there may be greater expansion in a direction perpendicular to the direction of longitudinally-extending slits 75 (for example, in the direction of the arrows shown in FIG. 26). It will be appreciated that the location and magnitude of expansion of generally cylindrical body 35 can be controlled by the number and location of longitudinally-extending slits 75, the configuration of enlargement 100, the configuration of generally cylindrical body 35 (e.g., its lumen 50 and the associated side wall of the cylindrical body 35 adjacent the lumen), etc. In one preferred form of the present invention, expansion of generally cylindrical body 35 occurs at the zone where distal end reservoir 55 meets short intermediate portion 60, with expansion occurring as enlargement 100 moves out of the comparatively larger diameter distal end reservoir 55 and into the comparatively smaller diameter intermediate portion 60.

Figure 28:
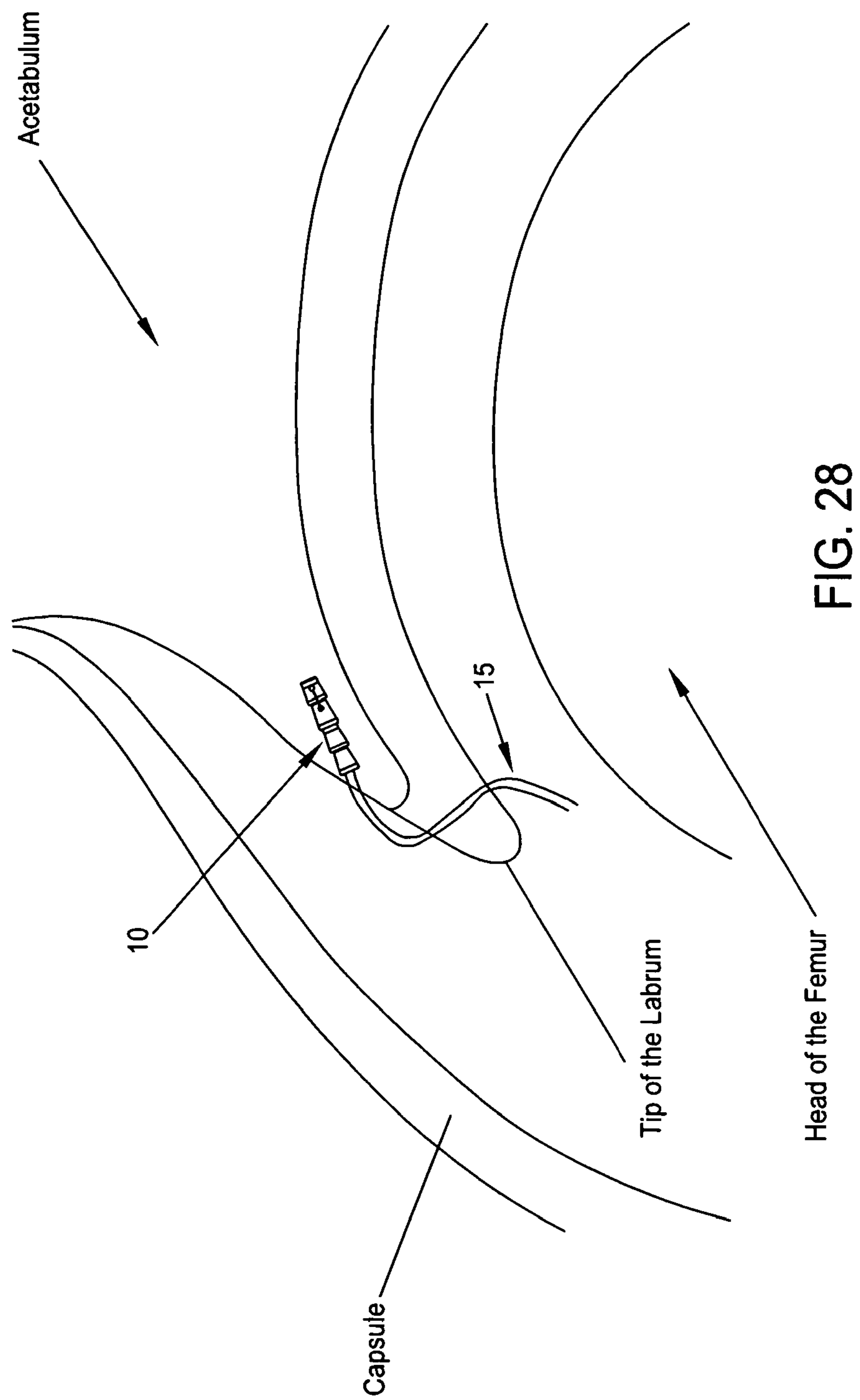
FIGS. 28 and 28A are schematic views showing the suture anchor system of FIGS. 19-27 being used to re-attach the labrum to the acetabulum.
Figure 28A:
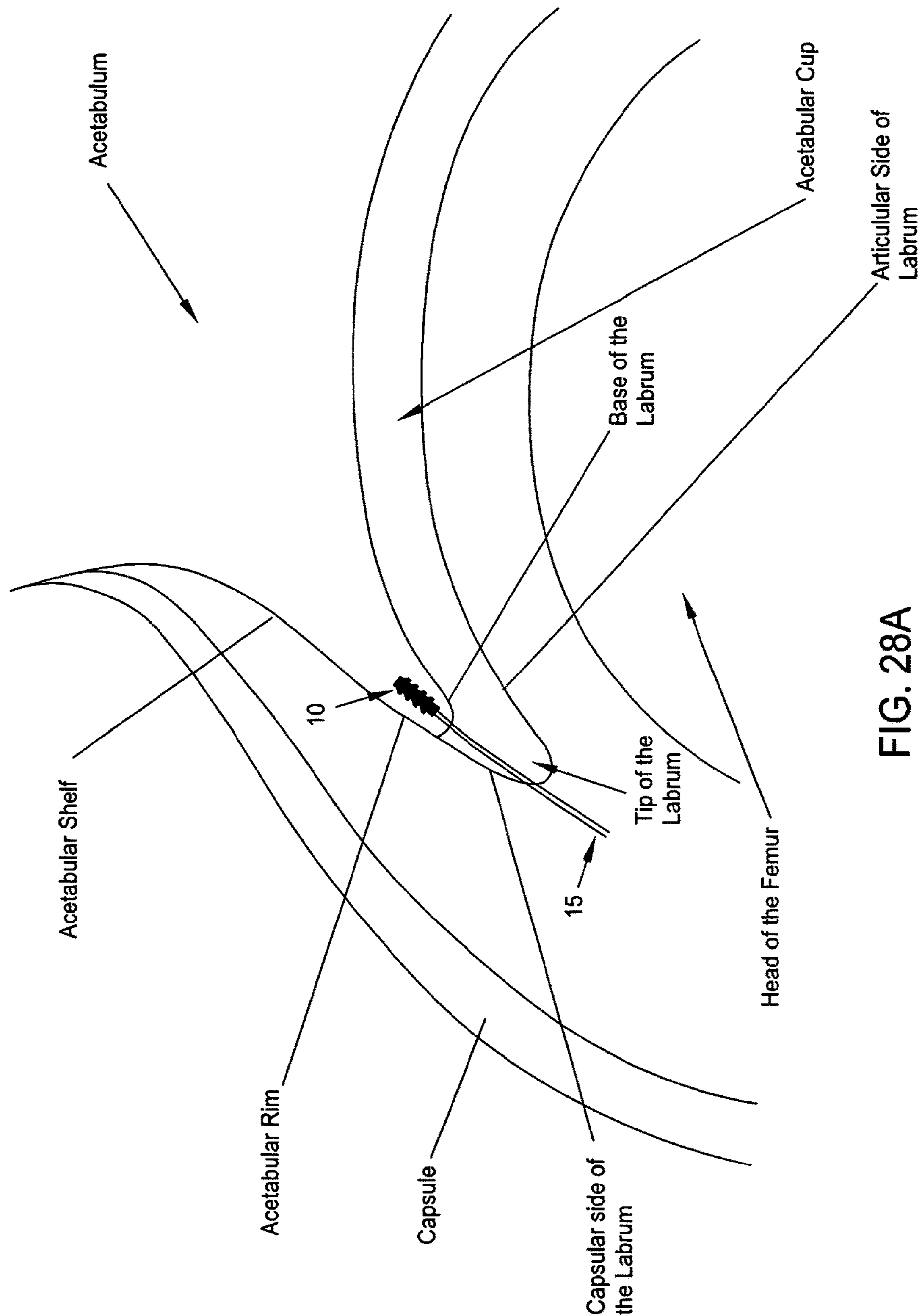

Significantly, in view of the modest holding power required to secure the labrum in place, anchor 10 can have a very small size, much smaller than a typical bone anchor of the sort used to hold a ligament in place. By way of example but not limitation, anchor 10 may have a length of 0.325 inches, an outer diameter (unexpanded) of 0.063 inches, and an outer diameter (expanded) of 0.080 inches. This small size enables a minimal puncture to be made in the labrum (and hence a minimal hole to be made in the labrum), thus reducing potential damage to the labral tissue and enabling a more accurate puncture location through the labrum. The small size of anchor 10 also allows the anchor to be placed closer to, or directly into, the rim of the acetabular cup, without fear of the anchor penetrating into the articulating surfaces of the joint. See, for example, FIG. 28, which shows anchor 10 placed close to the rim of the acetabular cup, and FIG. 28A, which shows anchor 10 placed directly into the rim of the acetabular cup. This significantly reduces, or entirely eliminates, the labrum eversion problems discussed above. Furthermore, the small size of the anchor significantly reduces trauma to the tissue of the patient.

Once anchor 10 has been set in the acetabulum, guide 25 is removed from the surgical site, leaving anchor 10 deployed in the acetabulum and suture 15 extending out through the labrum.

This process may then be repeated as desired so as to deploy additional anchors through the labrum and into the acetabulum, with each anchor having a pair of associated free suture ends extending out through the labrum.

Finally, the labrum may be secured to the acetabular cup by tying the labrum down to the acetabulum using the free suture ends emanating from the one or more anchors.

Figure 31:
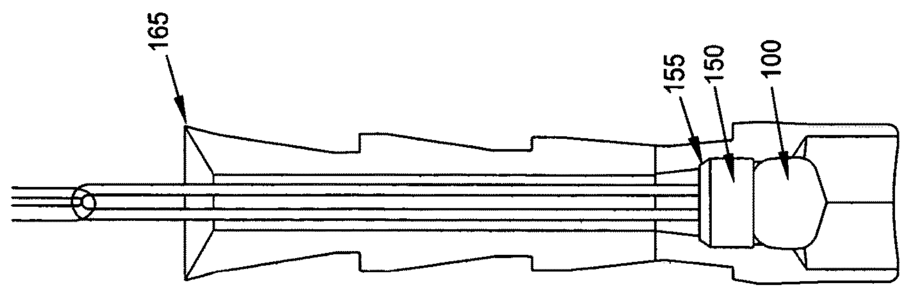
FIGS. 29-31 are schematic views showing an alternative form of the suture anchor system of the present invention.
Figure 30:
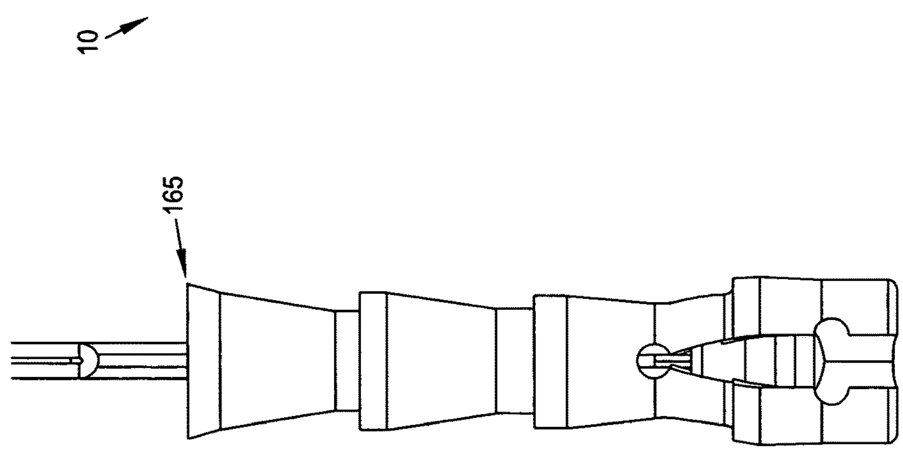
Figure 29:
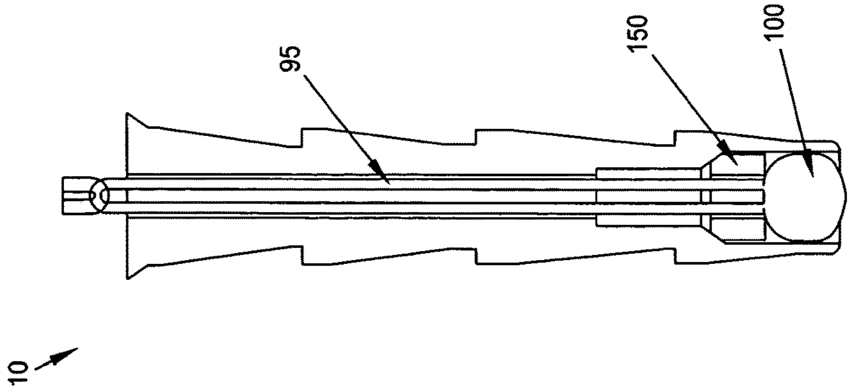

Some Alternative Constructions for the Novel Suture Anchor System of the Present Invention If desired, and looking now at FIGS. 29-31, a deployment cylinder 150 may be disposed on distal loop 95 of suture 15 just proximal to enlargement 100. Deployment cylinder 150 can be advantageous where enlargement 100 comprises a suture knot, since the deployment cylinder can ensure the uniform application of a radial expansion force to the wall of the anchor body even where the suture knot has a non-uniform configuration. Deployment cylinder 150 may have a beveled proximal end 155 to facilitate expansion of anchor 10 when suture 15 is pulled proximally. FIG. 29 depicts anchor 10 in an unexpanded state, while FIGS. 30-31 depict the anchor 10 in an expanded state.

Furthermore, one or more of the ribs 70 may utilize a different construction than that shown in FIGS. 21-23. More particularly, in FIGS. 21-23, each of the ribs 70 comprises a proximal portion which comprises a cylindrical surface 160. Such a cylindrical surface provides increased surface area contact for engaging the adjacent bone when anchor 10 is disposed in the acetabulum. However, if desired, one or more of the ribs 70 may terminate in a sharp proximal rim 165 (FIGS. 29-31) for biting into adjacent bone when suture 15 is pulled proximally.

Figure 32:
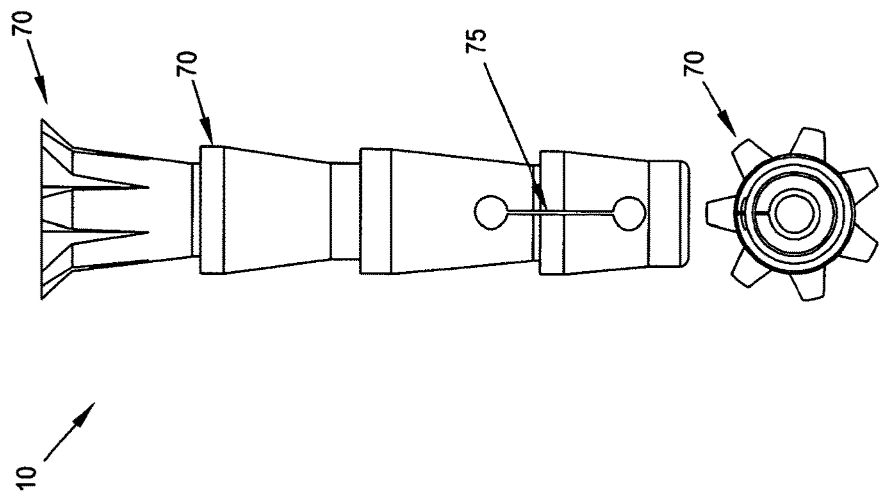
FIG. 32 is a schematic view showing another alternative form of the suture anchor system of the present invention.

Or one or more of the ribs 70 may be slotted as shown in FIG. 32 so as to provide a rib with increased flexibility. Such a construction can be useful since it allows the slotted rib 70 to be radially compressed so as to fit within inserter 20 and then radially expanded, in a spring-like manner, when deployed in the acetabulum.

Figure 33:
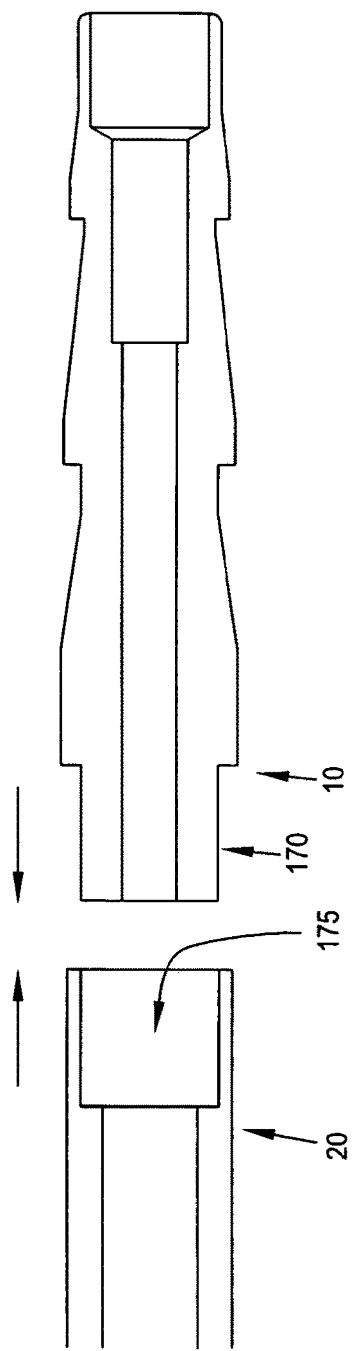
FIGS. 33-38 are schematic views showing alternative arrangements for coupling the anchor of the suture anchor system of FIGS. 19-27 to the inserter of the suture anchor system of FIGS. 19-27.
Figure 34:
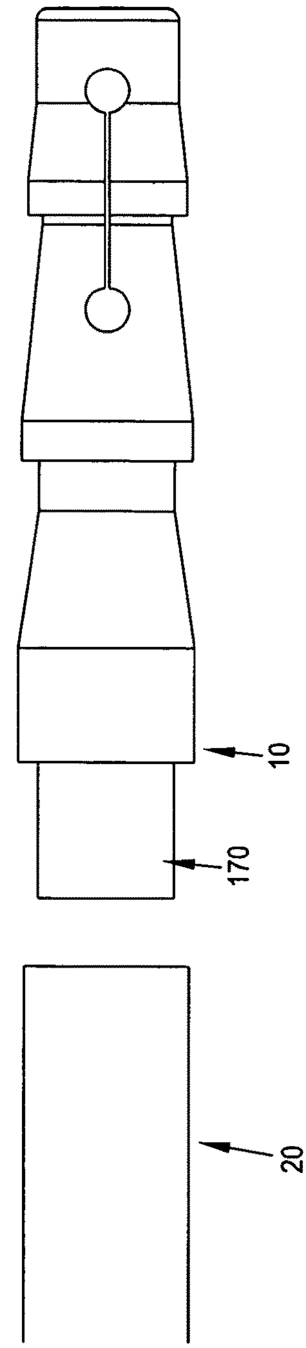
Figure 35:
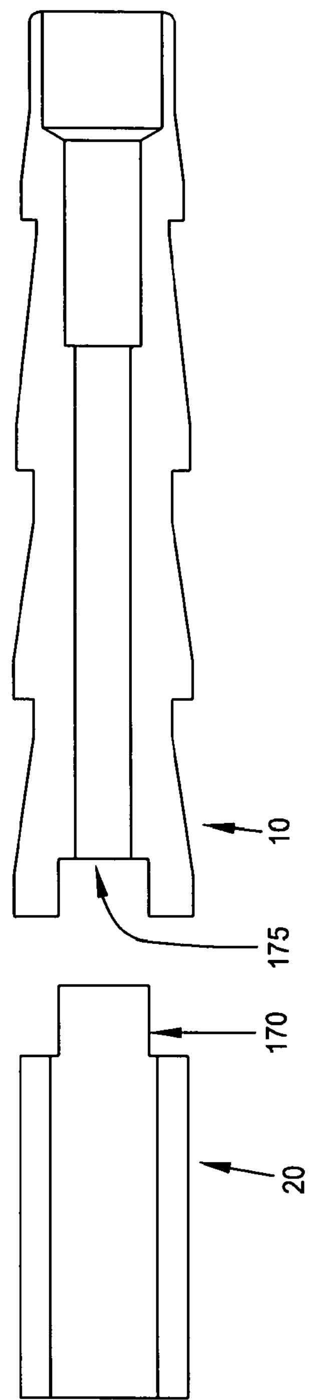
Figure 36:
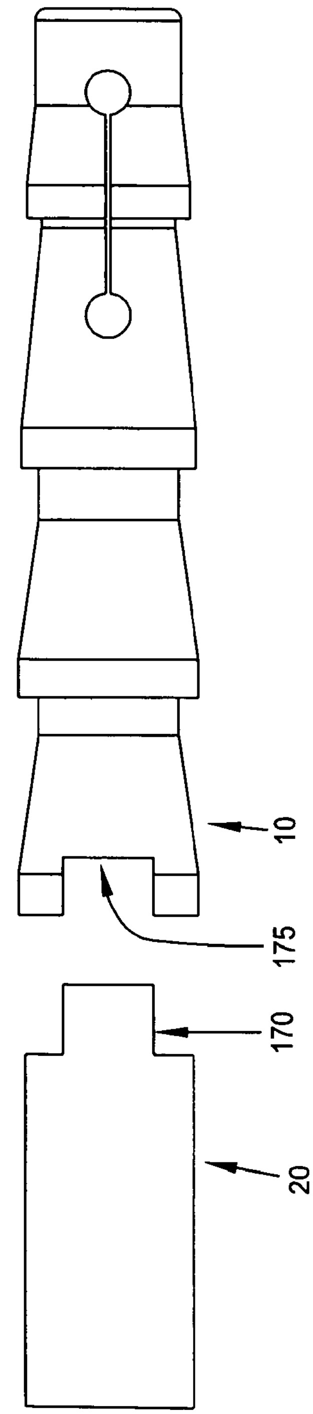
Figure 37:
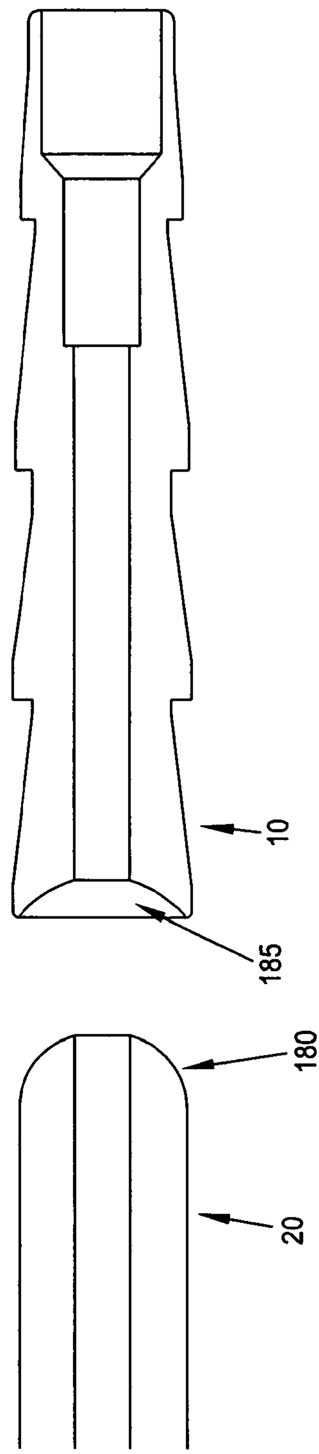
Figure 38:
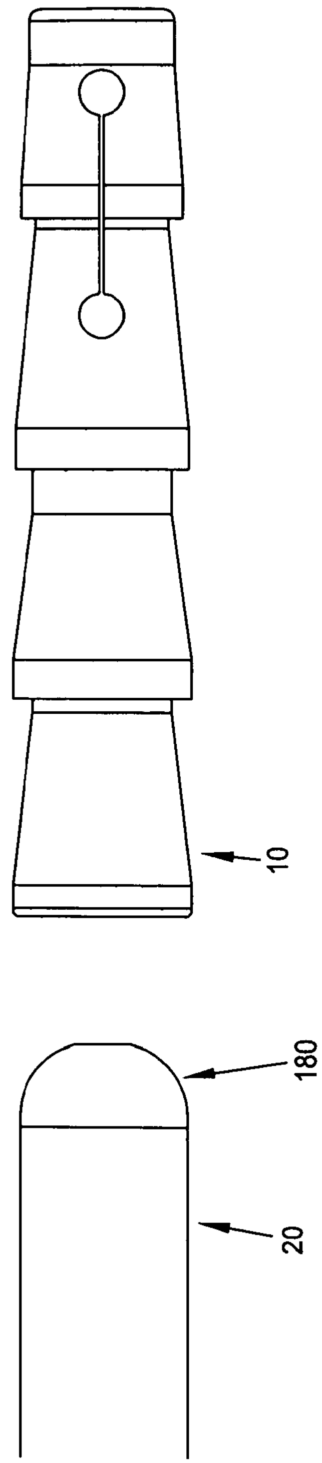

If desired, alternative arrangements can be provided for coupling anchor 10 to the distal end of inserter 20. More particularly, in FIGS. 33 and 34, a male-female connection is used to couple anchor 10 to inserter 20, with anchor 10 having a male projection 170 and inserter 20 having a corresponding female recess 175. In FIGS. 35 and 36, inserter 20 includes the male projection 170 and anchor 10 has the corresponding female recess 175. In FIGS. 37 and 38, inserter 20 has a convex surface 180 and anchor 10 has a corresponding concave surface 185. Still other constructions of this type will be apparent to those skilled in the art in view of the present disclosure.

Figures 39, 40, 41:
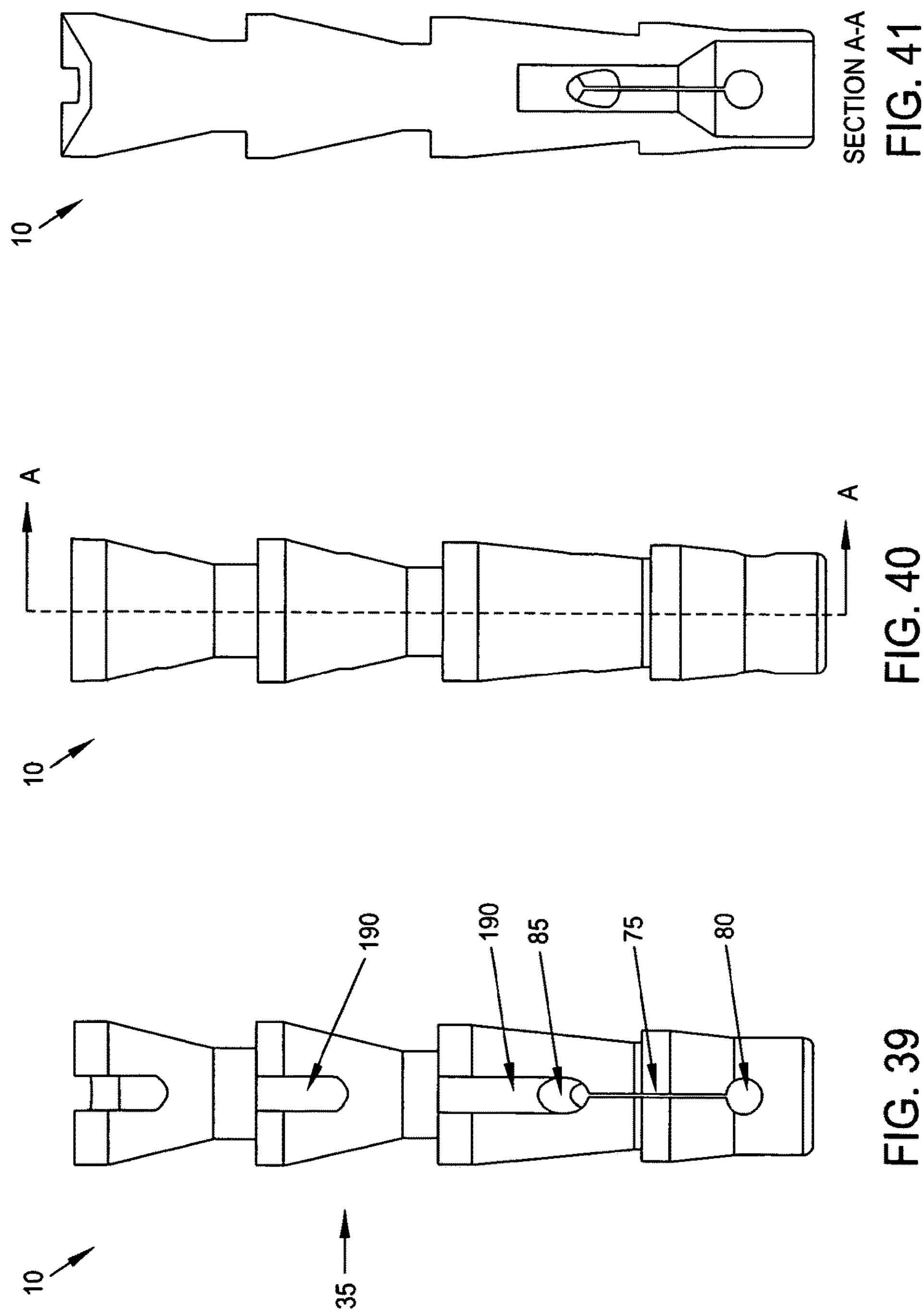
FIGS. 39-41 are schematic views showing still another alternative form of the suture anchor system of the present invention.

Looking next at FIGS. 39-41, in another form of present invention, suture 15 is intended to exit anchor 10 at proximal relief hole 85 and extend along the exterior of the generally cylindrical body 35. If desired, slots 190 may be provided in ribs 70 so as to accommodate suture 15 therein.

Figure 42:
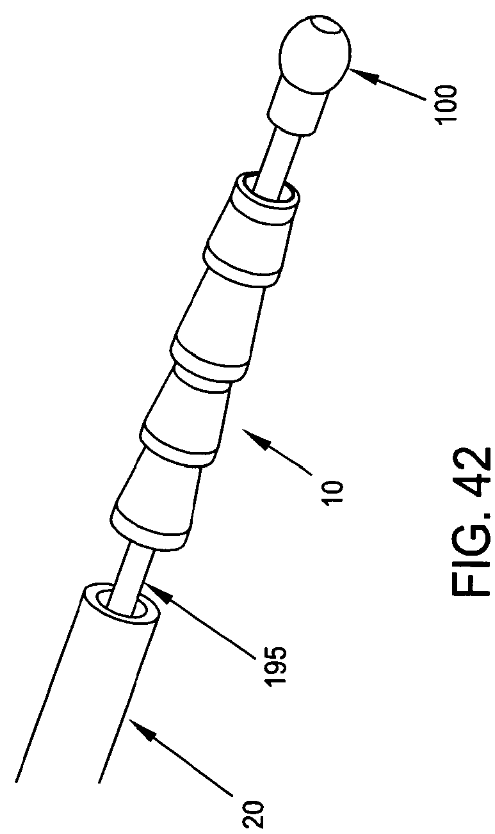
FIG. 42 is a schematic view showing yet another alternative form of the suture anchor system of the present invention.

In another form of the present invention, and looking now at FIG. 42, suture 15 can be replaced by a solid shaft 195. More particularly, solid shaft 195 extends through lumen 50 of anchor 10 and lumen 115 of inserter 20, and has enlargement 100 formed on its distal end. Proximal movement of solid shaft 195 causes enlargement 100 to expand the distal end of anchor 10 so as to cause anchor 10 to grip adjacent bone.

If desired, one or both of distal relief hole 80 and proximal relief hole 85 may be omitted, with longitudinally-extending slit 75 terminating in a blind surface at one or both ends.

Figures 43, 44, 45:
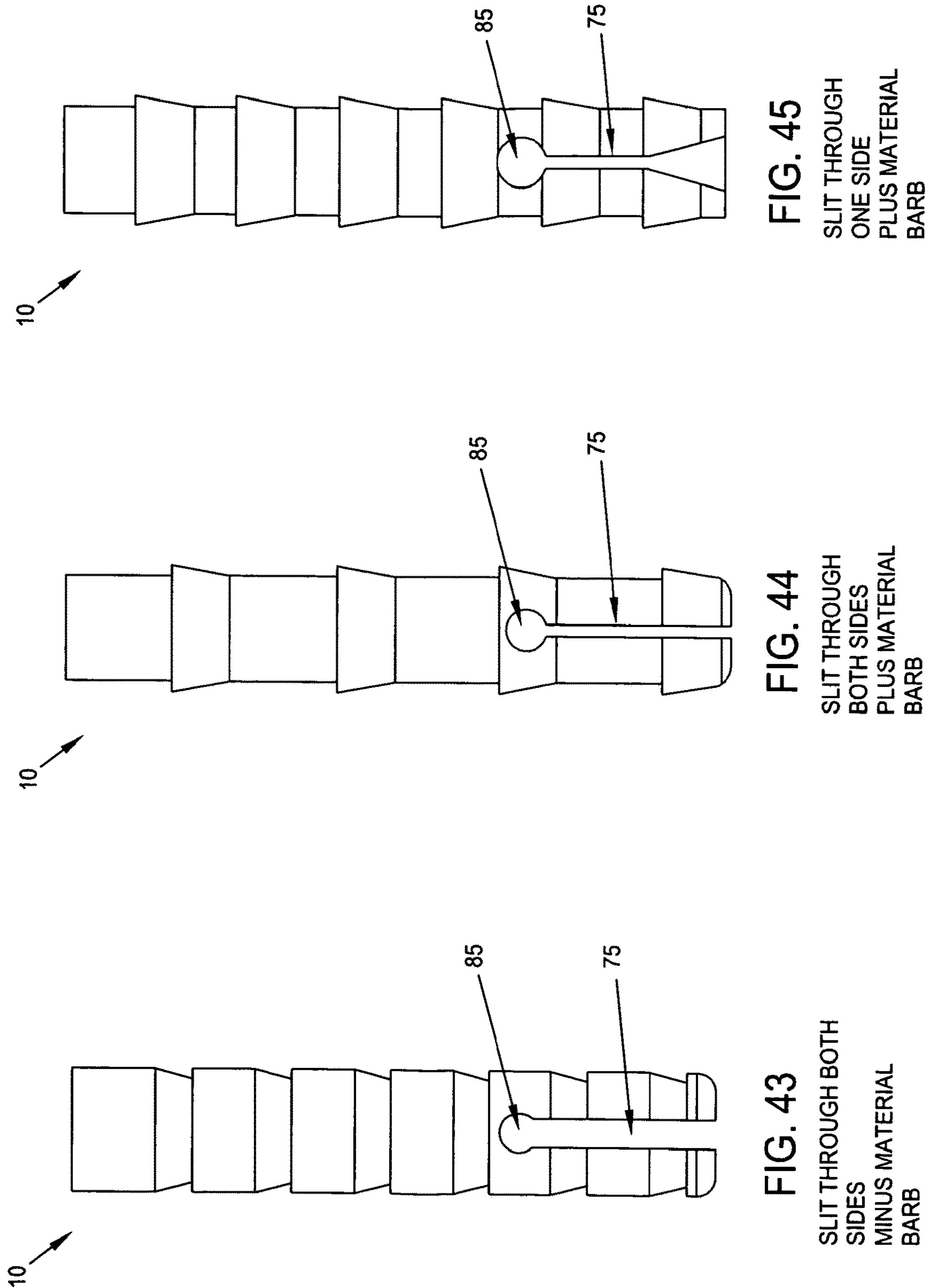
FIGS. 43-45 are schematic views showing another alternative form of the suture anchor system of the present invention.

Furthermore, if desired more than one longitudinally-extending slit 75 may be provided in anchor 10, e.g., two diametrically-opposed longitudinally-extending slits 75 may be provided. Additionally, if desired, longitudinally-extending slit 75 may extend all the way to the distal end of the anchor body, rather than stopping short of the distal end of the anchor body. See, for example, FIGS. 43 and 44, which show two diametrically-opposed, longitudinally-extending slits 75, wherein the slits extend all the way to the distal end of anchor 10, and with the two figures showing examplary rib configurations. See also FIG. 45, which shows an anchor 10 having a single longitudinally-extending slit 75, wherein the slit extends all the way to the distal end of the anchor.

Figure 48:
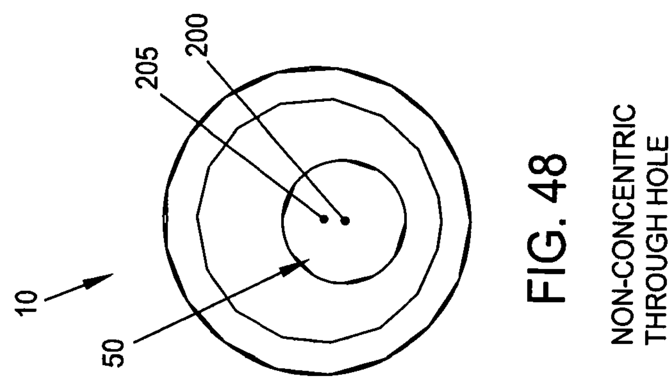
FIGS. 46-48 are schematic views showing still another alternative form of the suture anchor system of the present invention.
Figure 47:
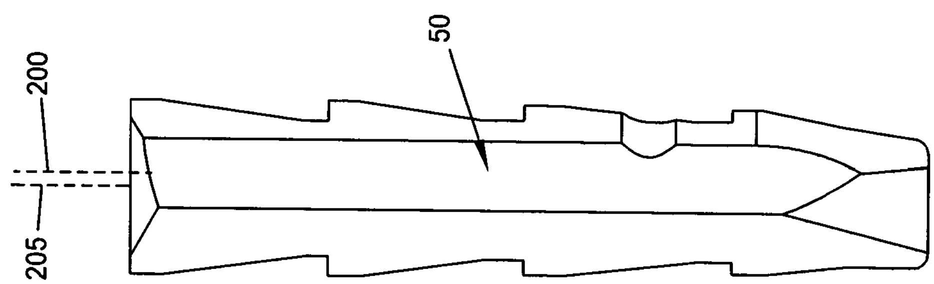
Figure 46:
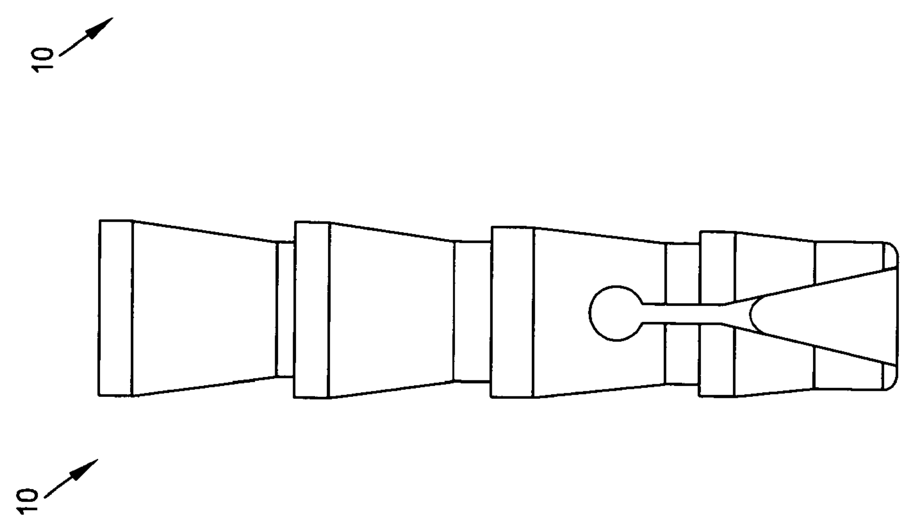

If desired, and looking now at FIGS. 46-48, lumen 50 may extend along a longitudinal axis 200 which is eccentric to the longitudinal axis 205 of generally cylindrical body 35. Such an eccentric construction can provide a thinner side wall on one side of the anchor and a thicker side wall on another side of the anchor, so as to create preferential body expansion.

Figure 49:
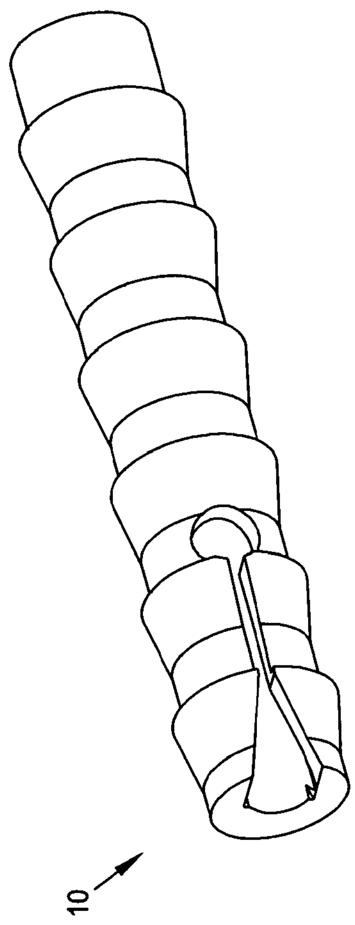
FIGS. 49-50 are schematic views showing yet another alternative form of the suture anchor system of the present invention.
Figure 50:
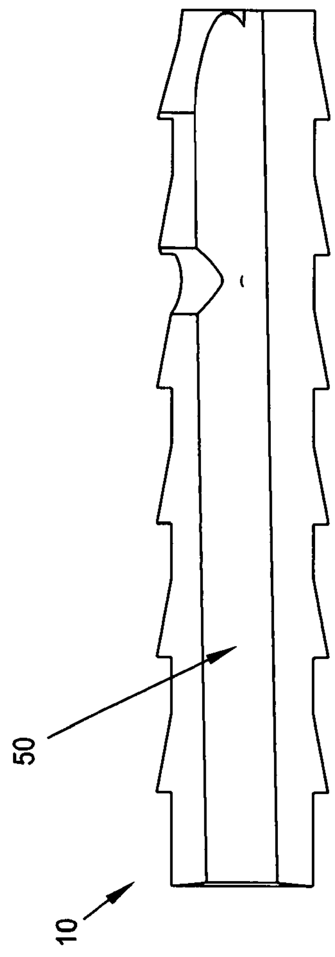

Or anchor 10 may be provided with an angled through-hole to create varying wall thicknesses and non-symmetric effects as shown in FIGS. 49 and 50.

Figure 51:
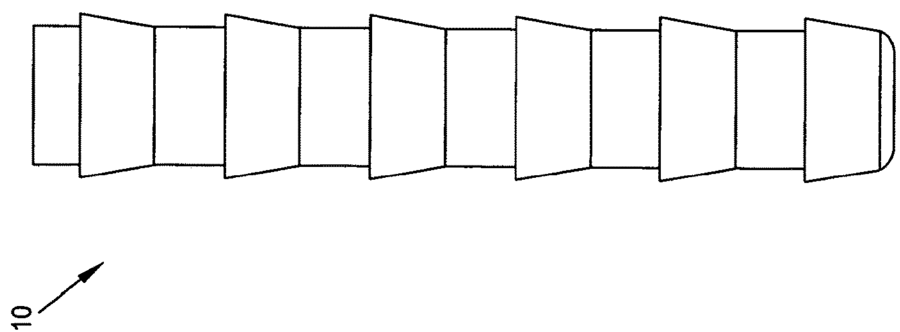
FIG. 51 is a schematic view showing another alternative form of the suture anchor system of the present invention.
Figure 54:
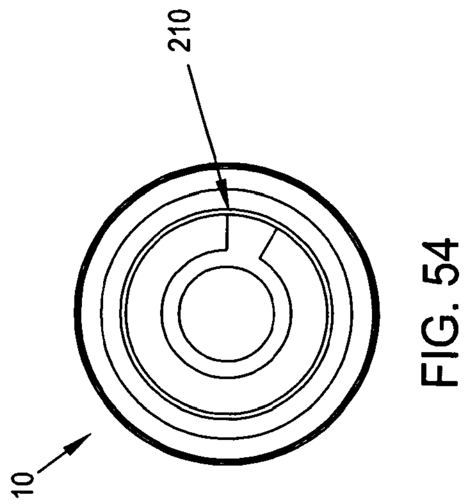
FIGS. 52-54 are schematic views showing still another alternative form of the suture anchor system of the present invention.
Figure 53:
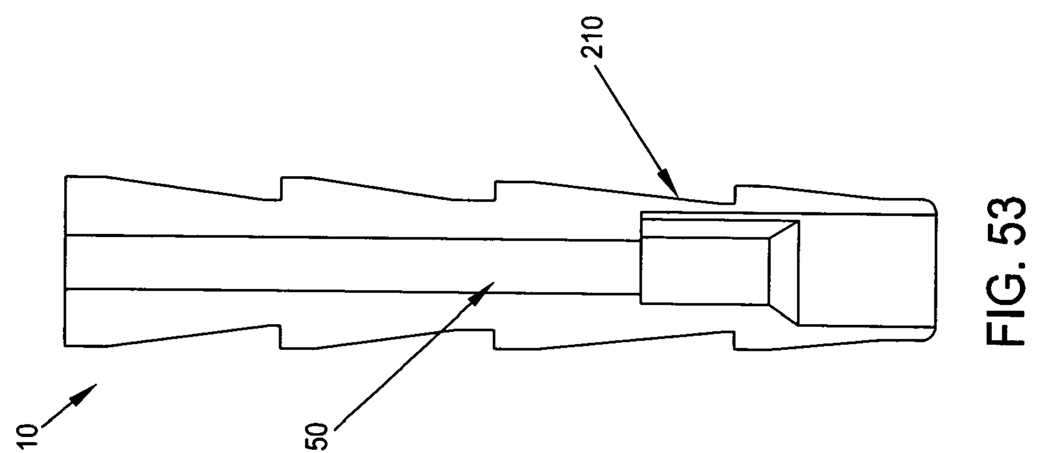
Figure 52:
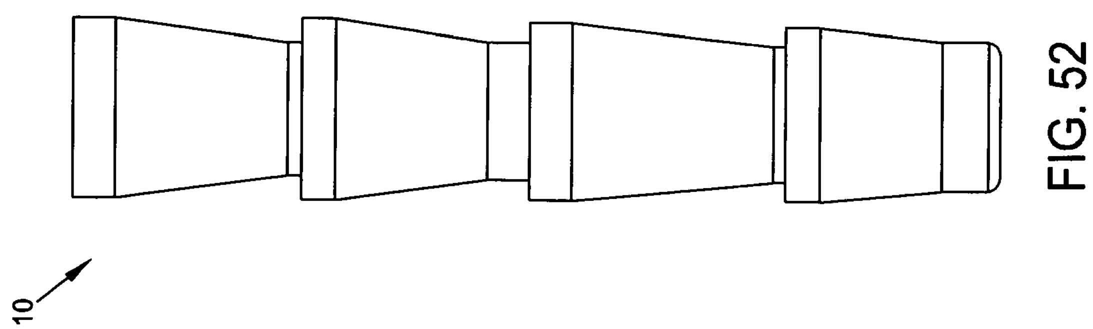
Figure 55:
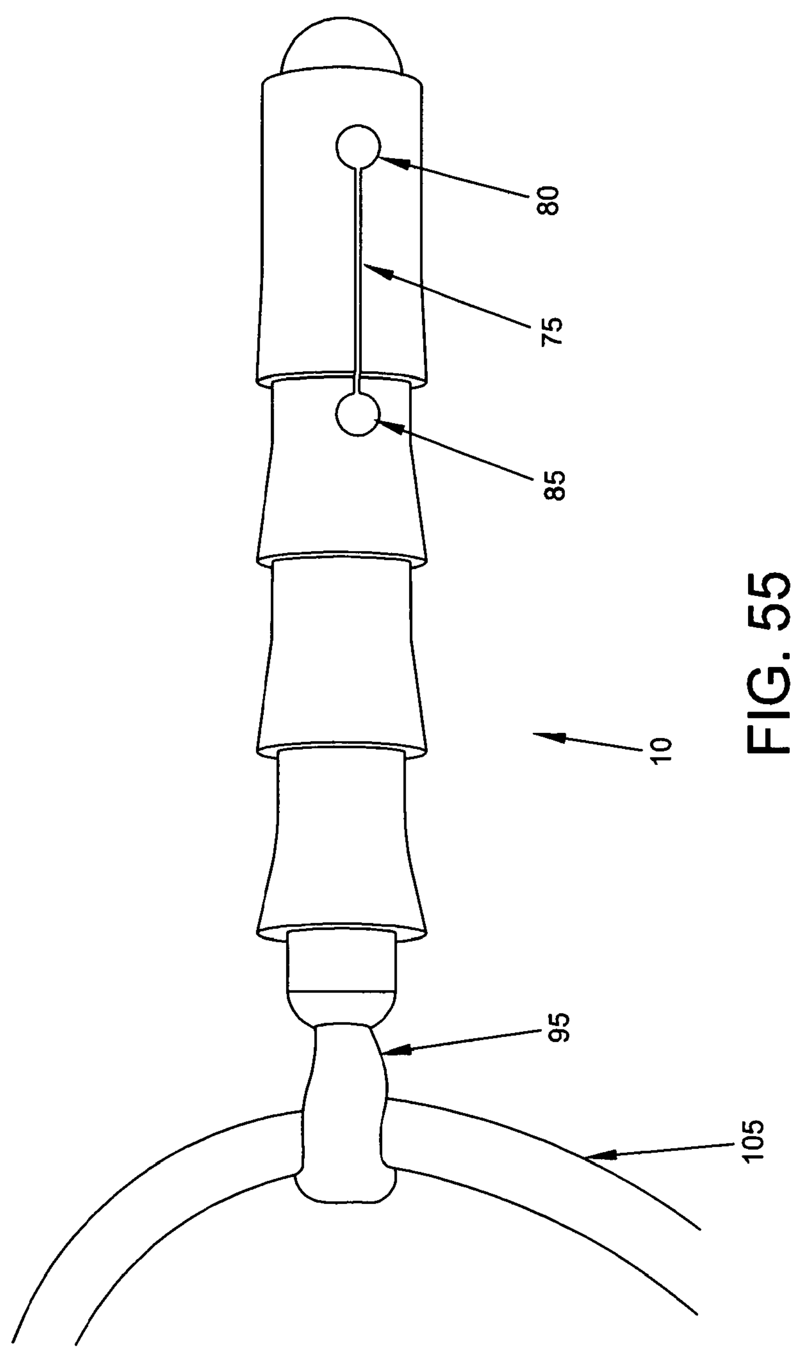
FIGS. 55-60 are schematic views showing yet another alternative form of the present invention.
Figure 56:
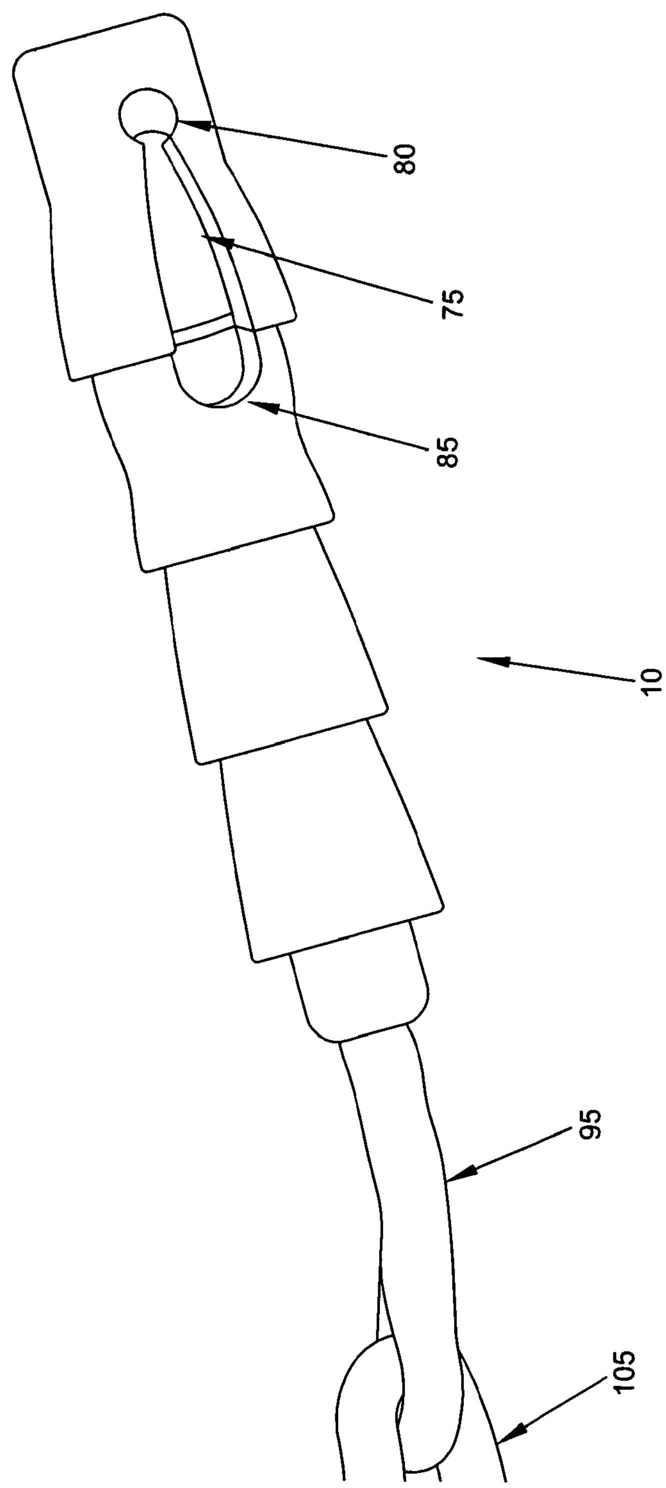
Figure 57:
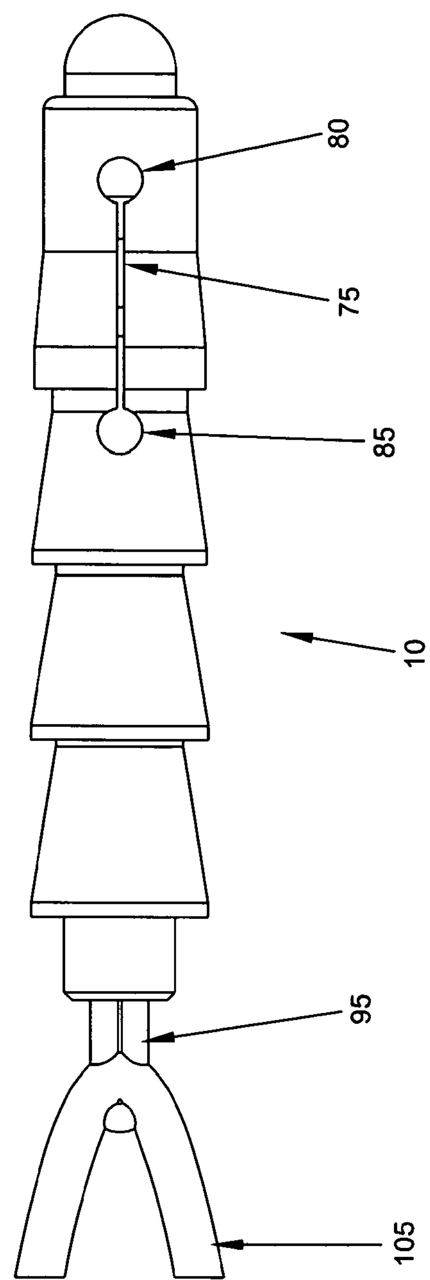
Figure 58:
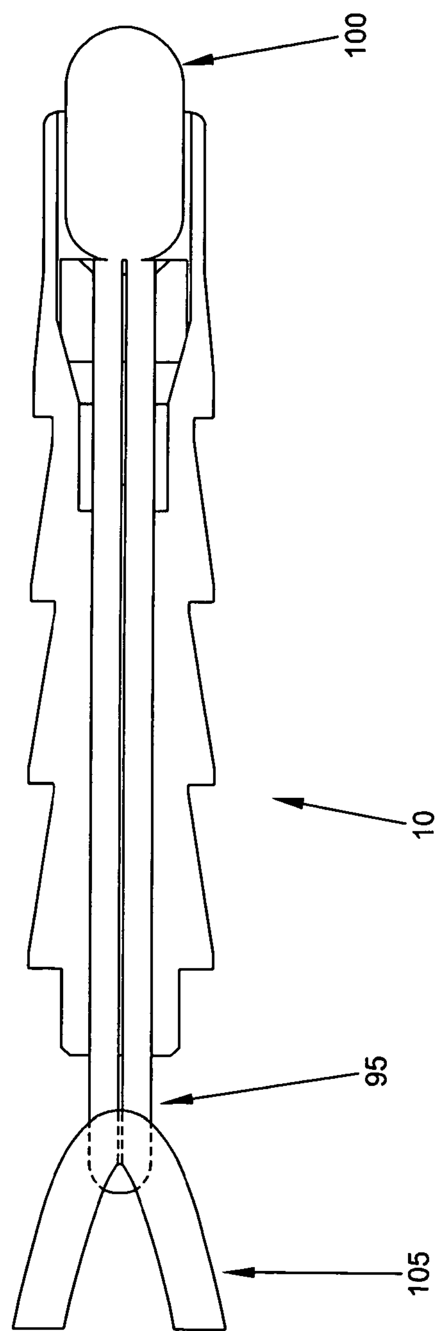
Figure 59:
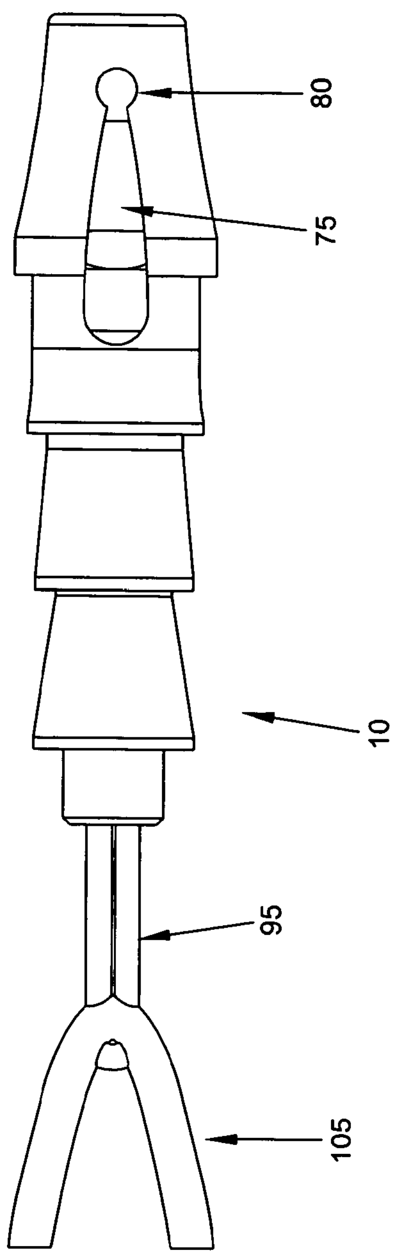
Figure 60:
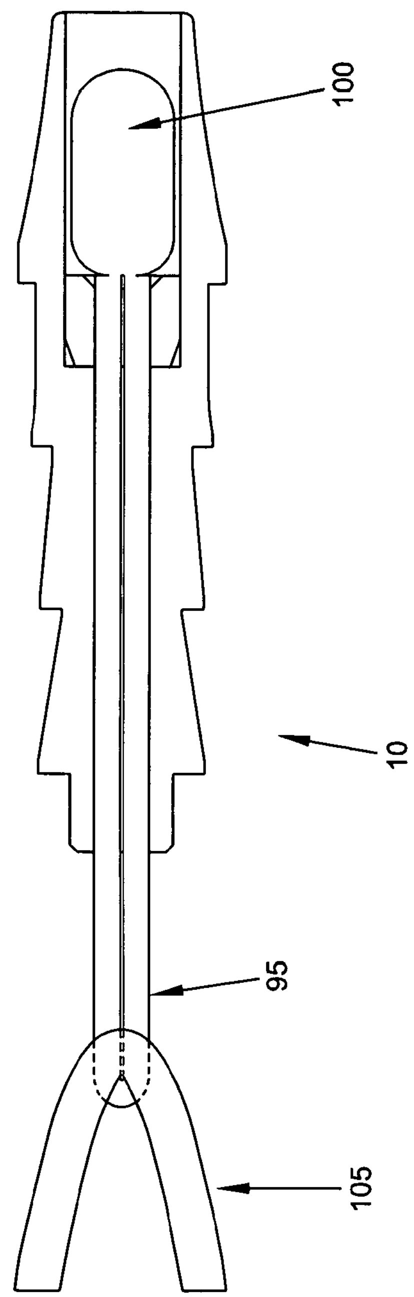

If desired, and looking now at FIG. 51, anchor 10 can be constructed so that longitudinally-extending slit 75 is omitted entirely. In this form of the invention, anchor 10 is preferably formed with one or more thin-walled sections 210 (FIGS. 52-54) which fracture when enlargement 100 is forced proximally.

Alternatively, in another form of the invention, anchor 10 is constructed so that its generally cylindrical body 35 expands radially when enlargement 100 moves proximally, but the distal end of the anchor does not split open. See FIGS. 55-58. Again, the direction and extent of the expansion of cylindrical body 35 may be controlled by the number and location of the longitudinally-extending slits 75, the configuration of enlargement 100, the configuration of generally cylindrical body 35 (e.g., its lumen 50 and the associated side wall of the cylindrical body 35 adjacent the lumen), etc.

Additional Construction Details

Anchor 10 can be made out of any material consistent with the present invention, e.g., anchor 10 can be made out of a biocompatible plastic (such as PEEK), an absorbable polymer (such as poly-L-lactic acid, PLLA), bio-active materials such as hydrogels, or metal (such as stainless steel or titanium).

Suture 15 can be made out of any material consistent with the present invention, e.g., common surgical suture materials. One such material is woven polymer such as PE or UHMWPE. Another material is a co-polymer material such as UHMWPE/polyester. Yet another material is an absorbable polymer such as polyglycolic acid, polylactic acid, polydioxanone, or caprolactone. Proximal loop 105 is preferably a #1 suture size; alternatively, it is a #2 suture size, a #0 suture size, or a #2-0 suture size. Distal loop 95 is preferably a #2-0 suture size; alternatively, it is a #2 suture size, a #1 suture size, or a #0 suture size.

Figure 1A:
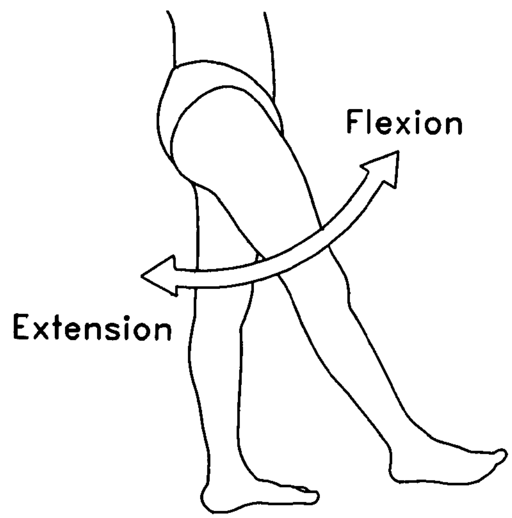
FIGS. 1A-1D are schematic views showing various aspects of hip motion.
Figure 1B:
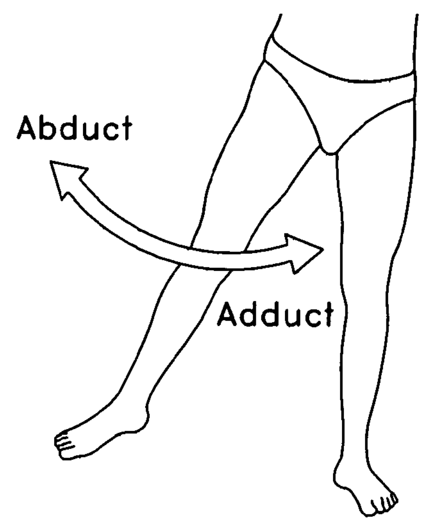
Figure 1C:
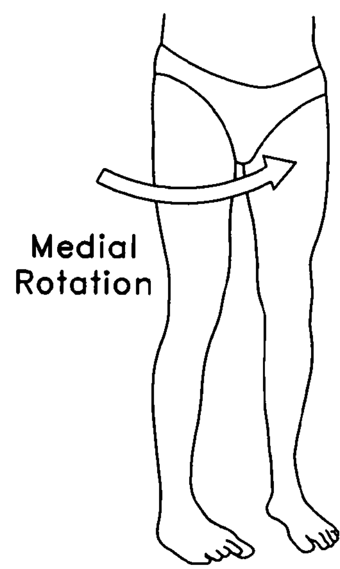
Figure 1D:
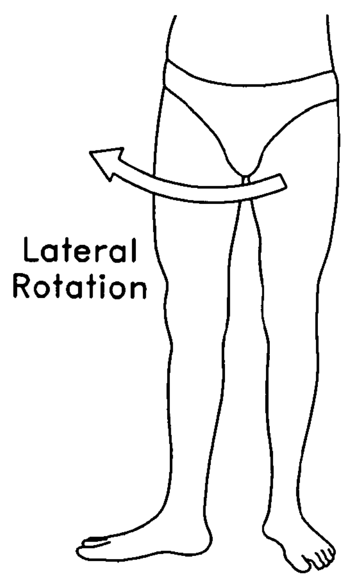
Figure 2:
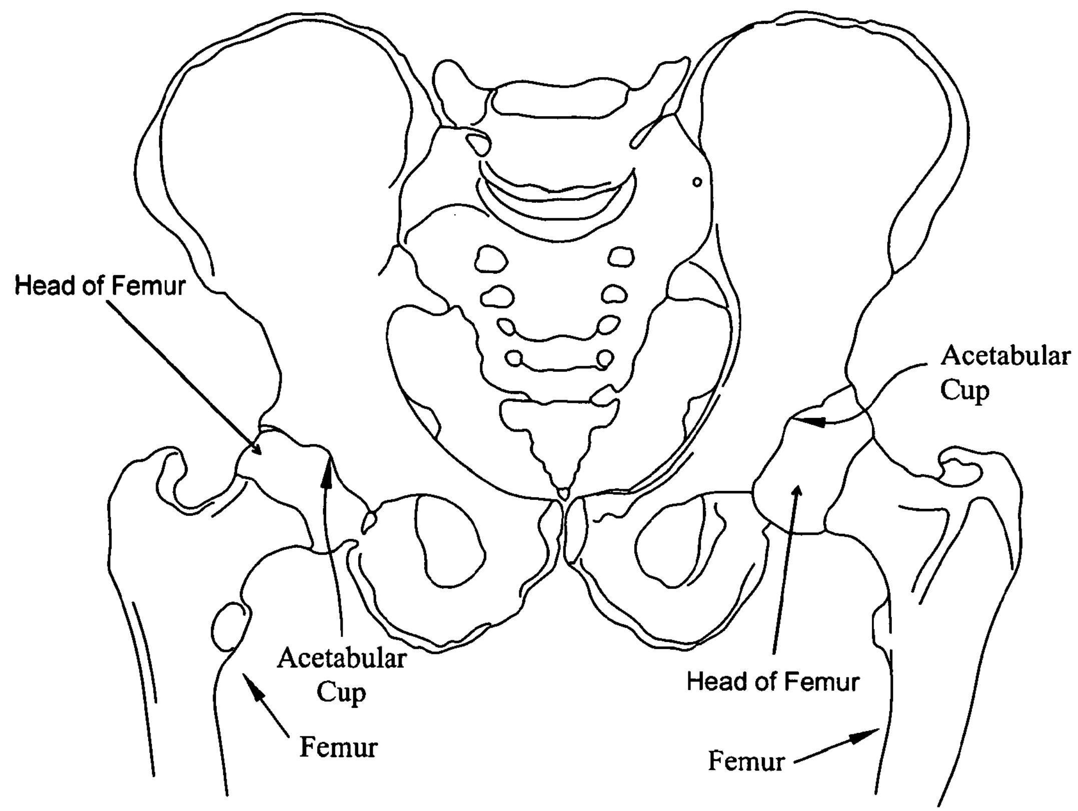
FIG. 2 is a schematic view showing bone structures in the region of the hip joint.
Figure 3:
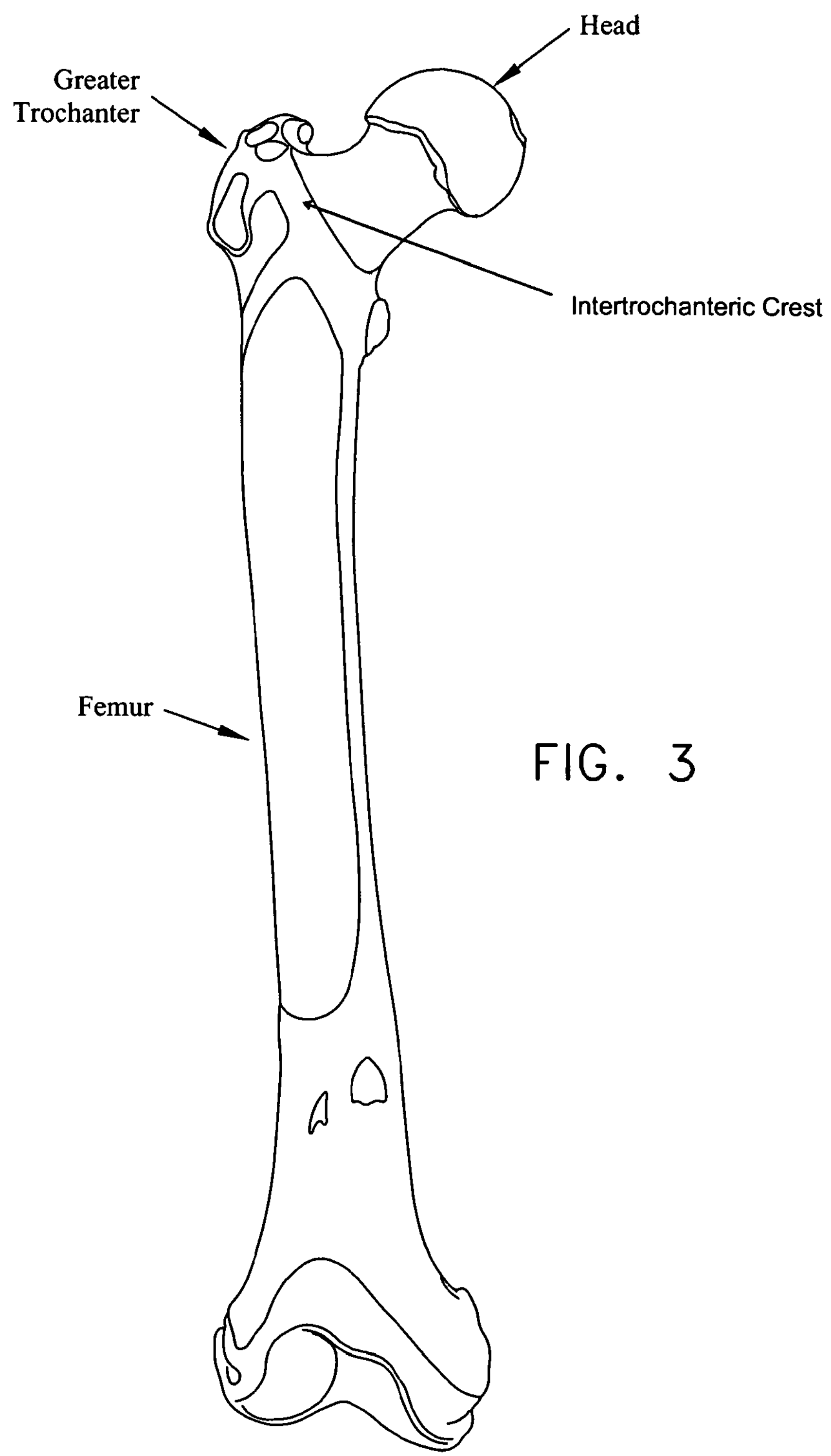
FIG. 3 is a schematic anterior view of the femur.
Figure 4:
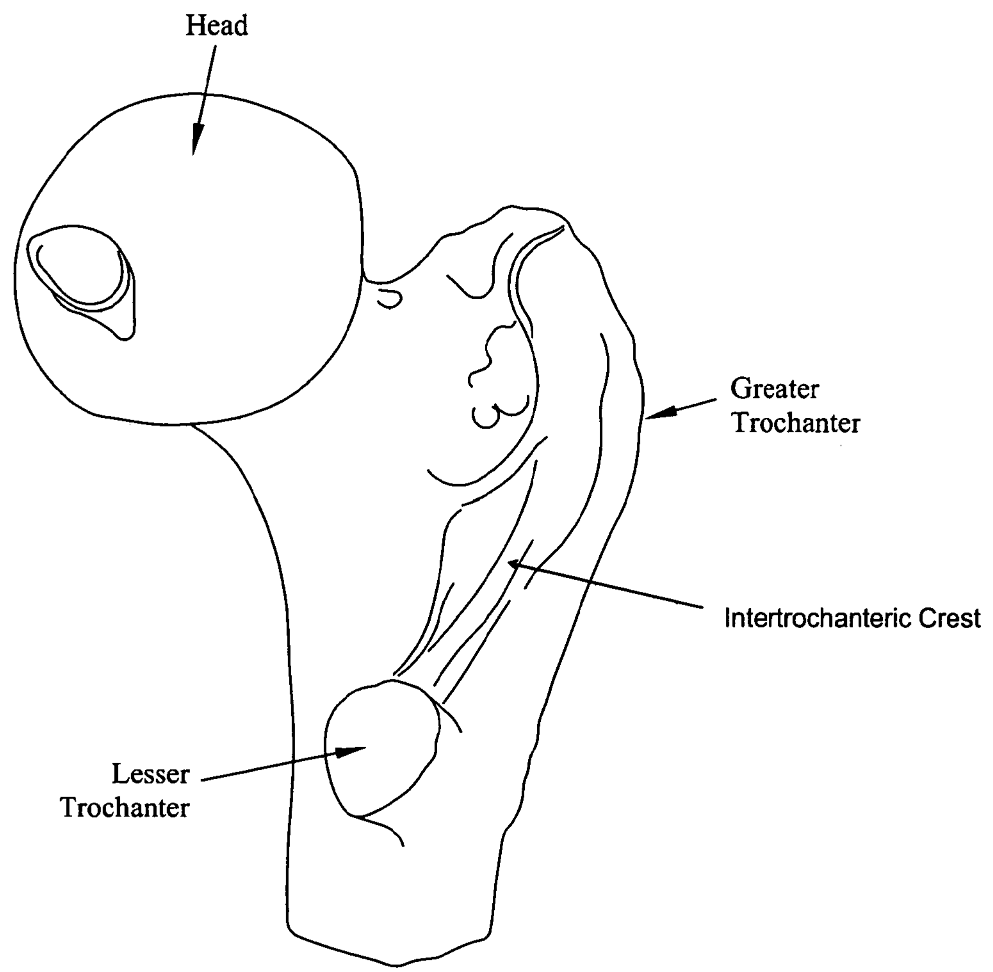
FIG. 4 is a schematic posterior view of the top end of the femur.
Figure 5:
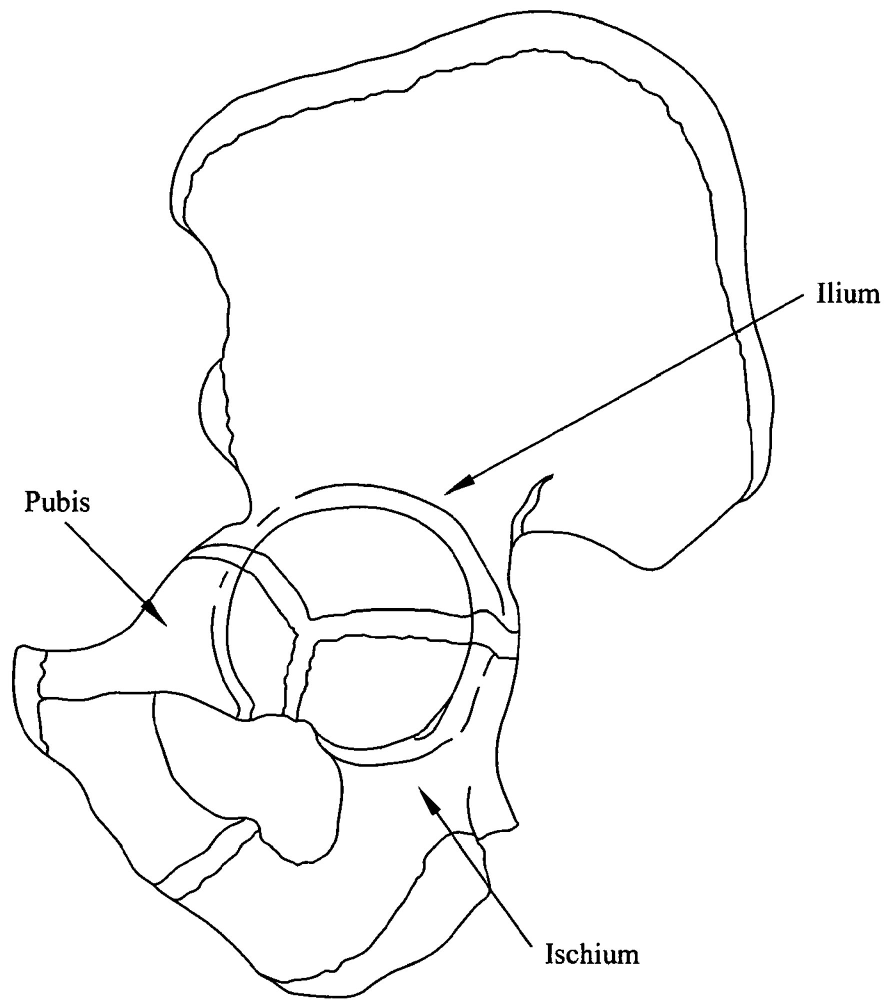
FIG. 5 is a schematic view of the pelvis.
Figure 6:
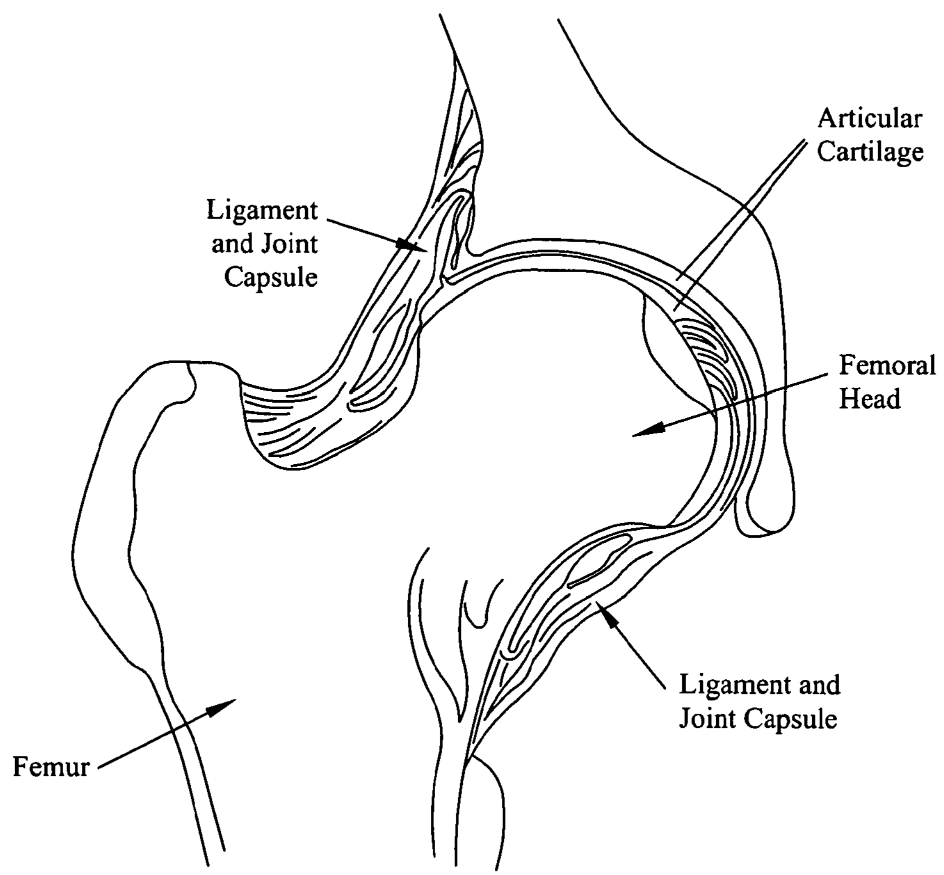
FIGS. 6-12 are schematic views showing bone and soft tissue structures in the region of the hip joint.
Figure 7:
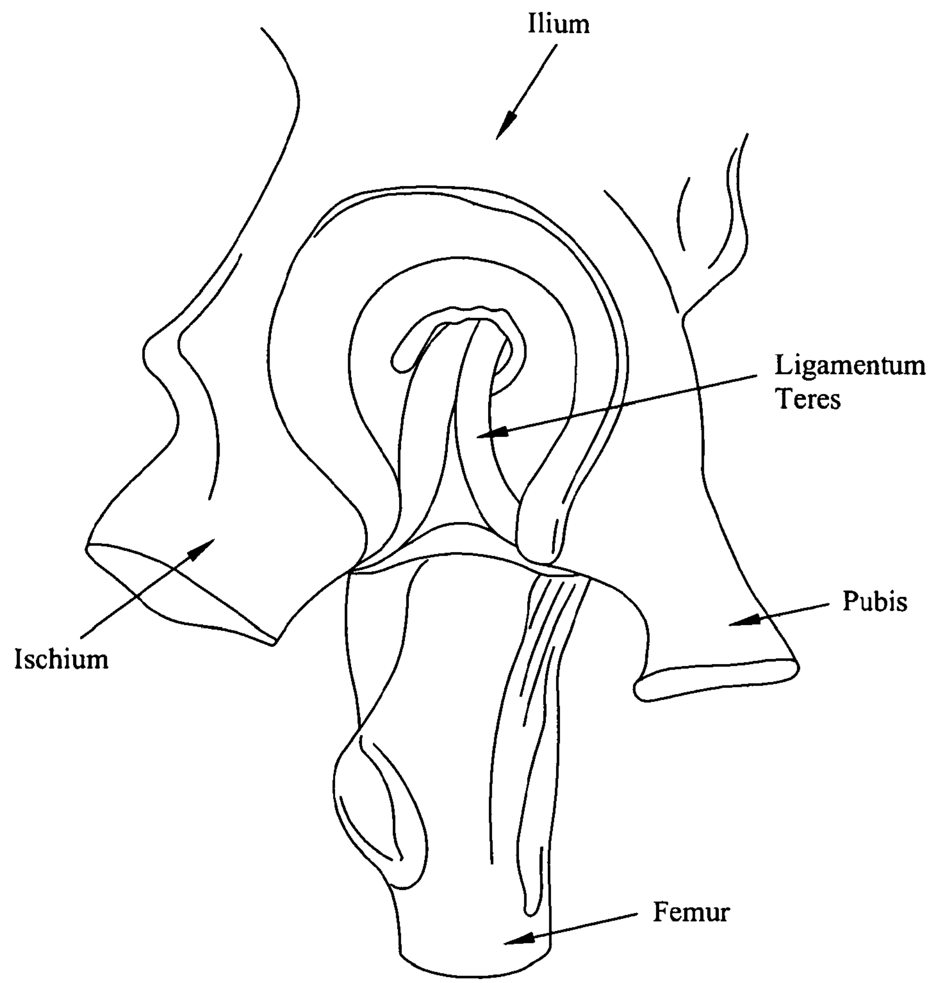
Figure 8:
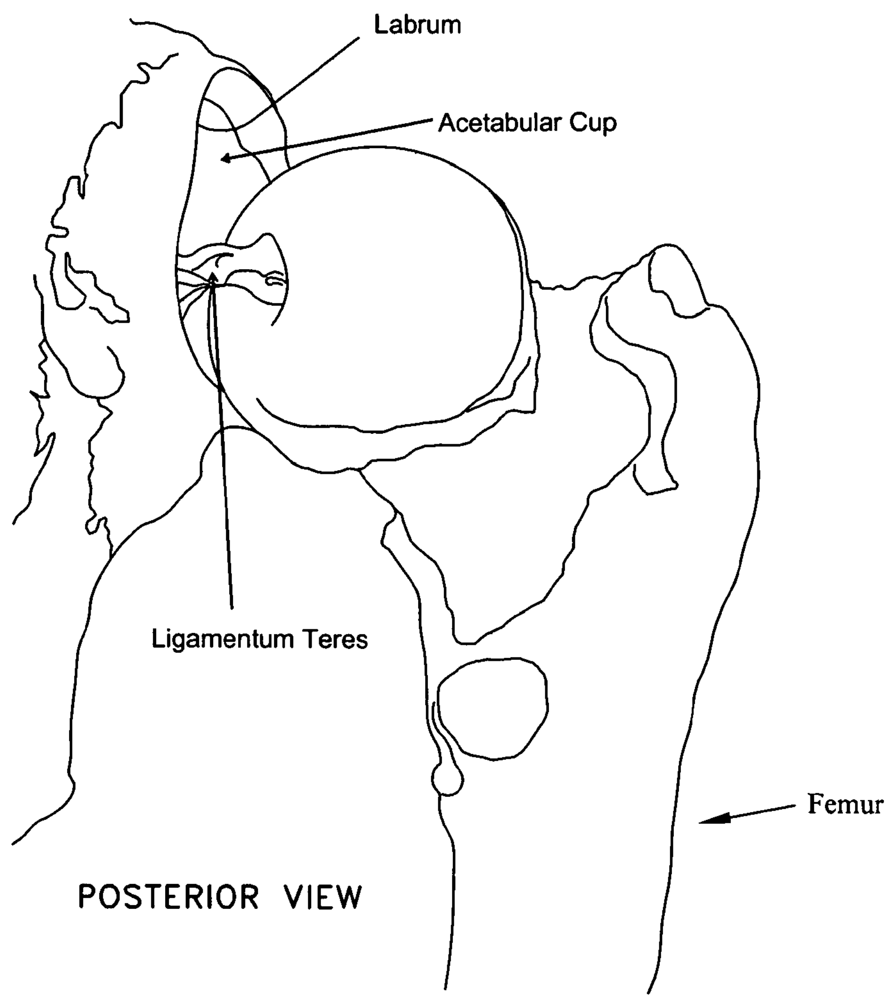
Figure 9:
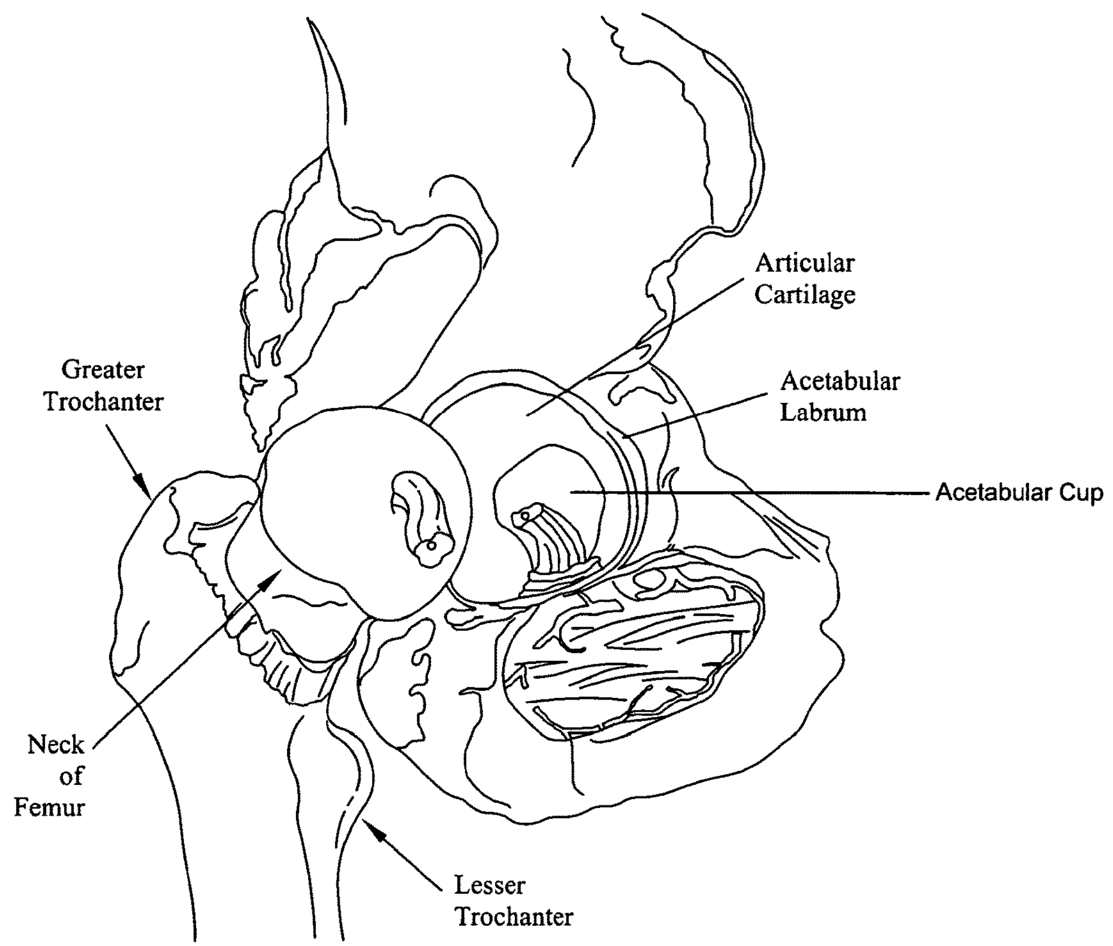
Figure 10:
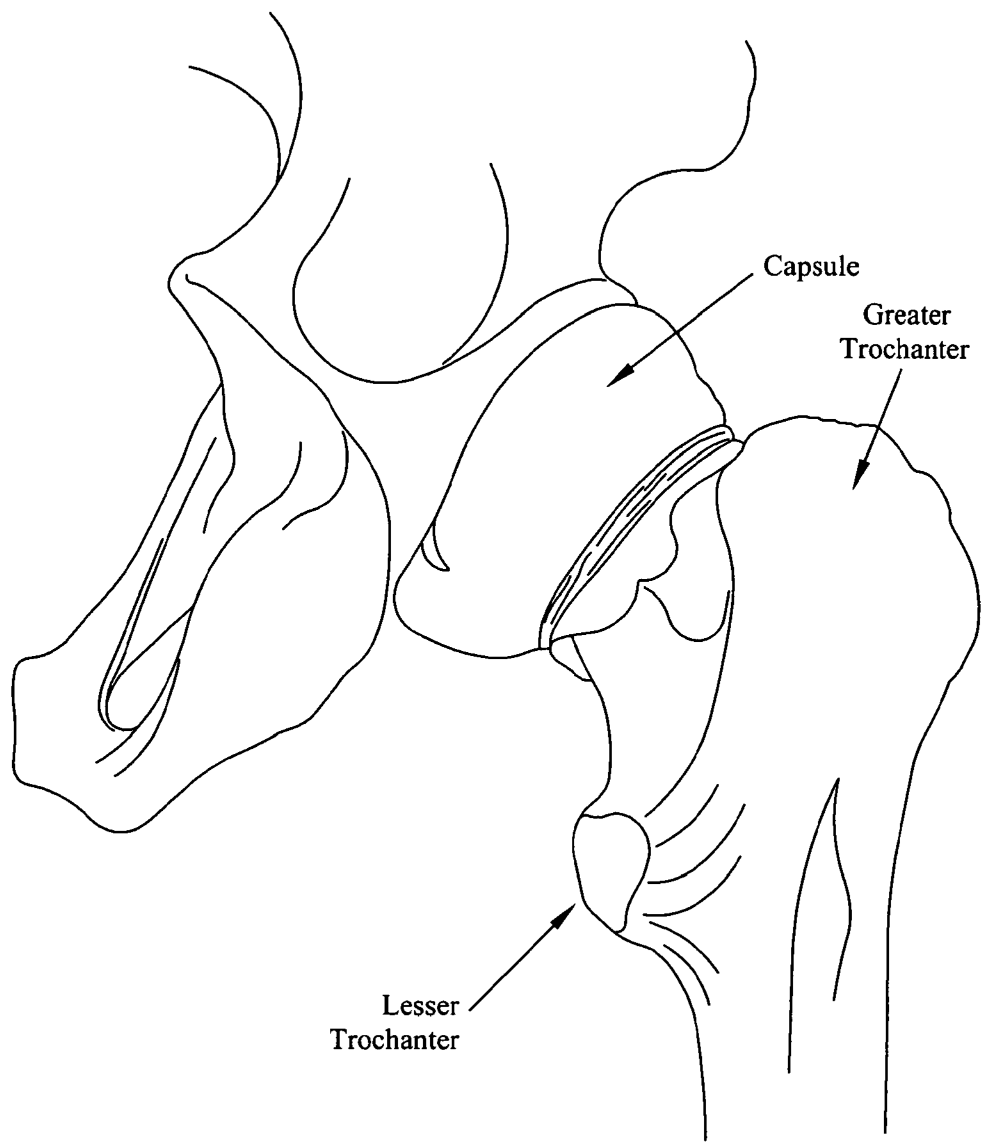
Figure 11:
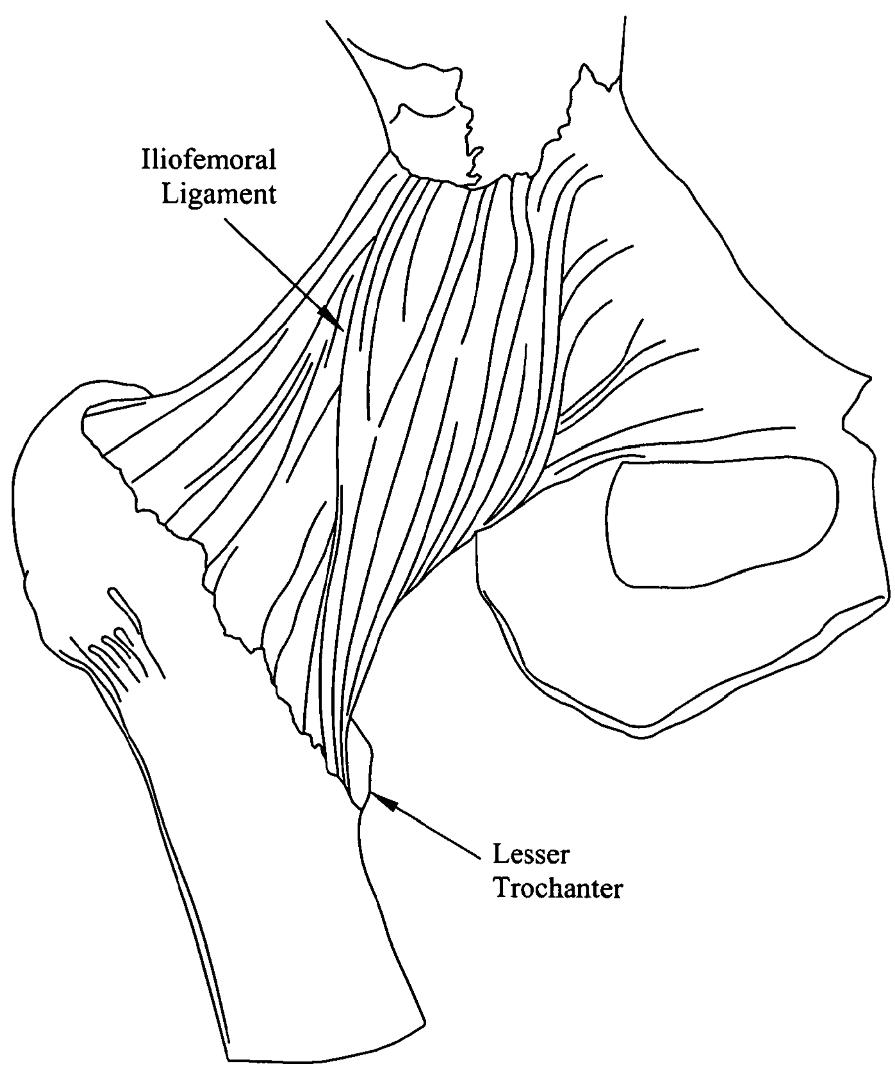
Figure 12:
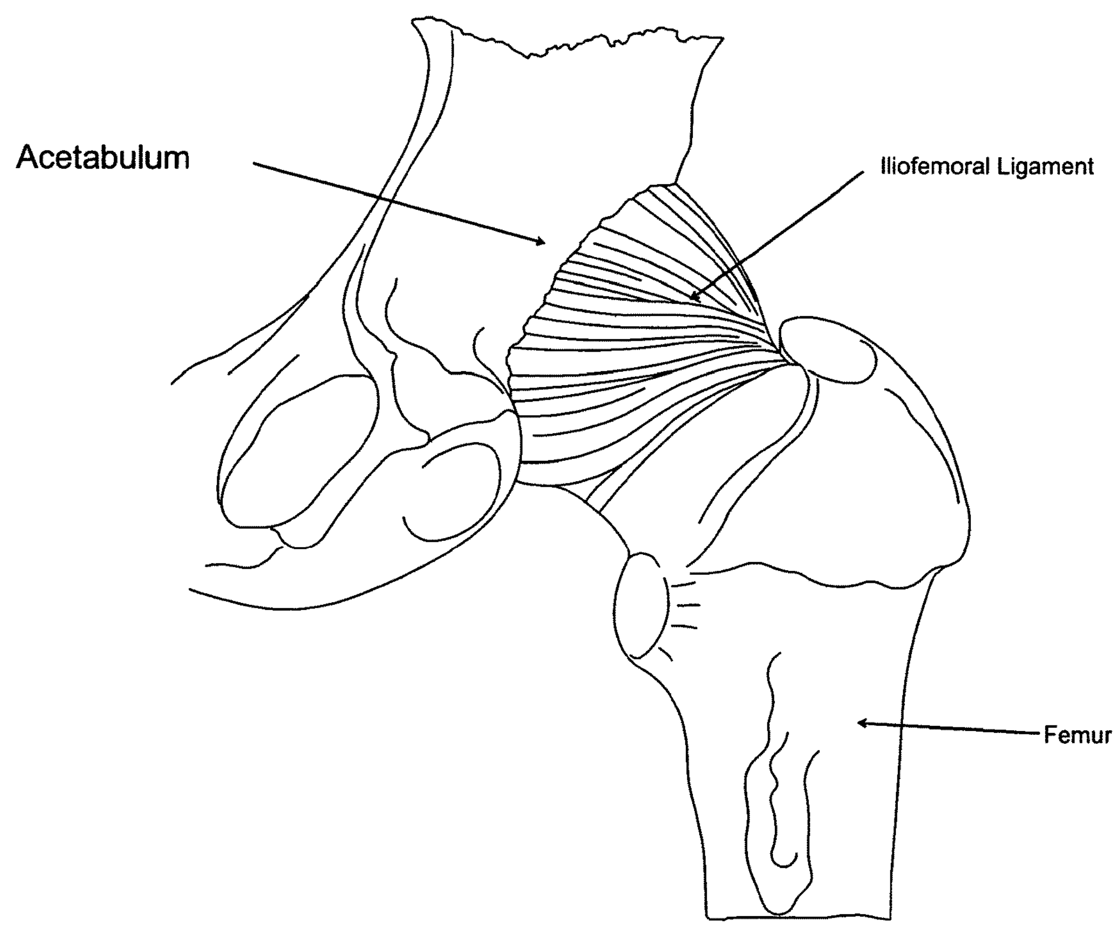
Figure 13:
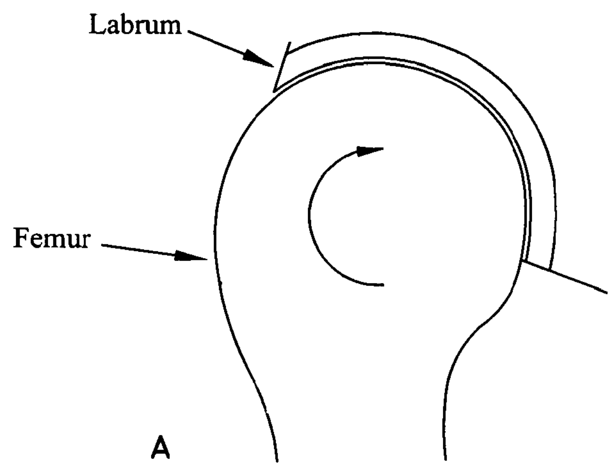
FIG. 13 is a schematic view showing cam-type femoroacetabular impingement (i.e., cam-type FAI)
Figure 13:
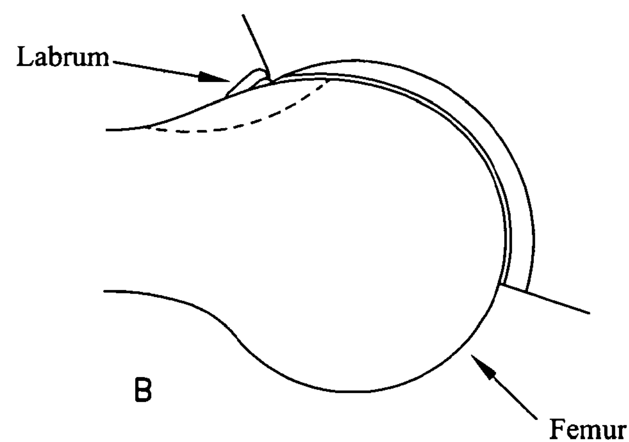
Figure 14:
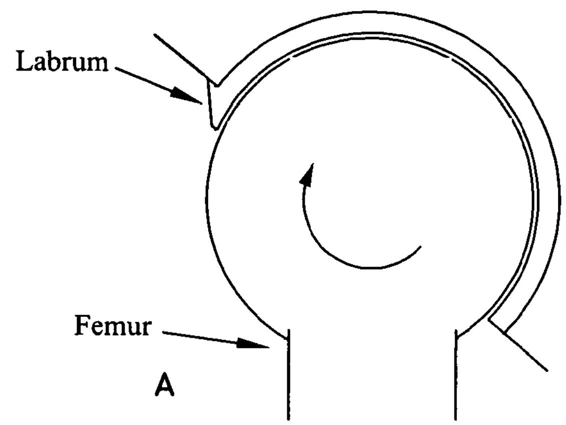
FIG. 14 is a schematic view showing pincer-type femoroacetabular impingement (i.e., pincer-type FAI)
Figure 14:
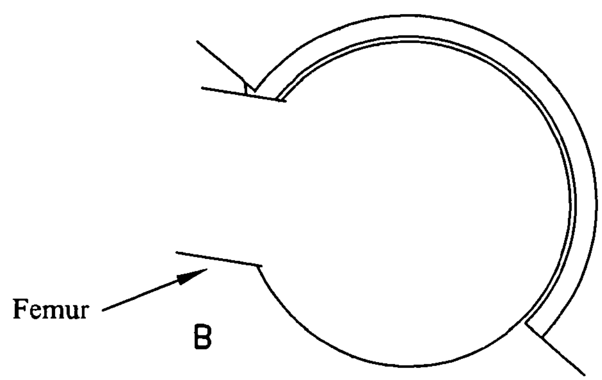
Figure 15:
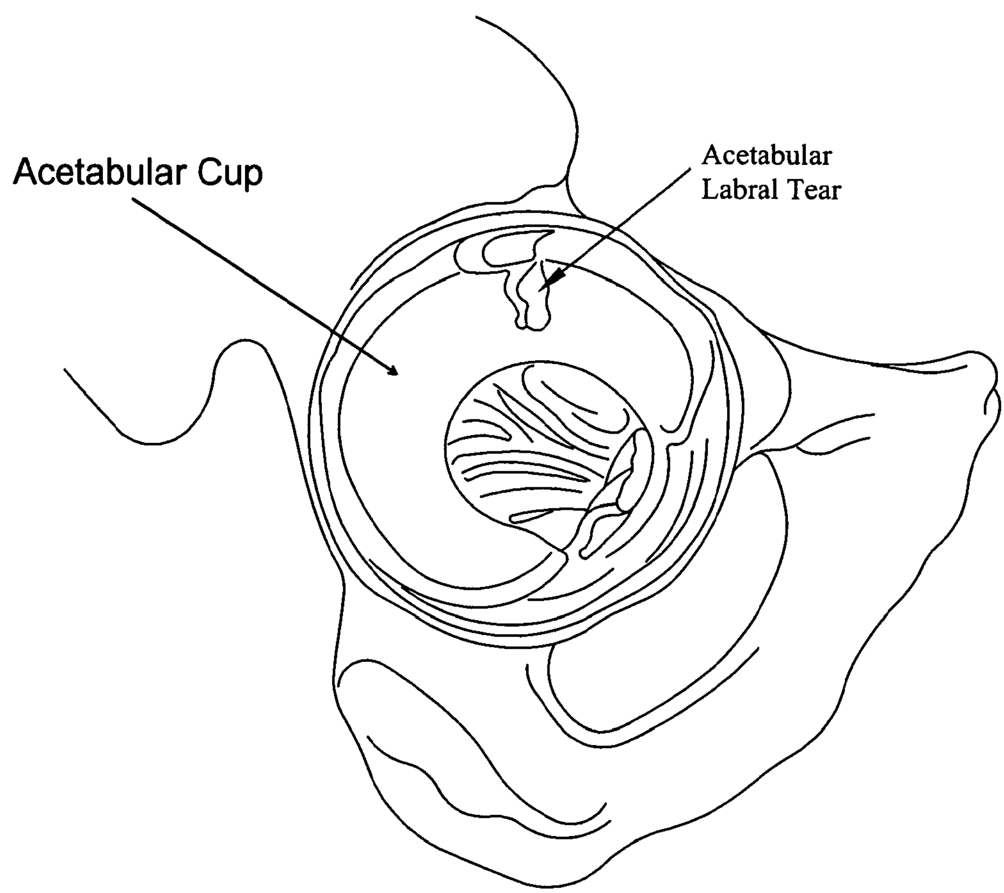
FIG. 15 is a schematic view showing a labral tear.
Figure 16:
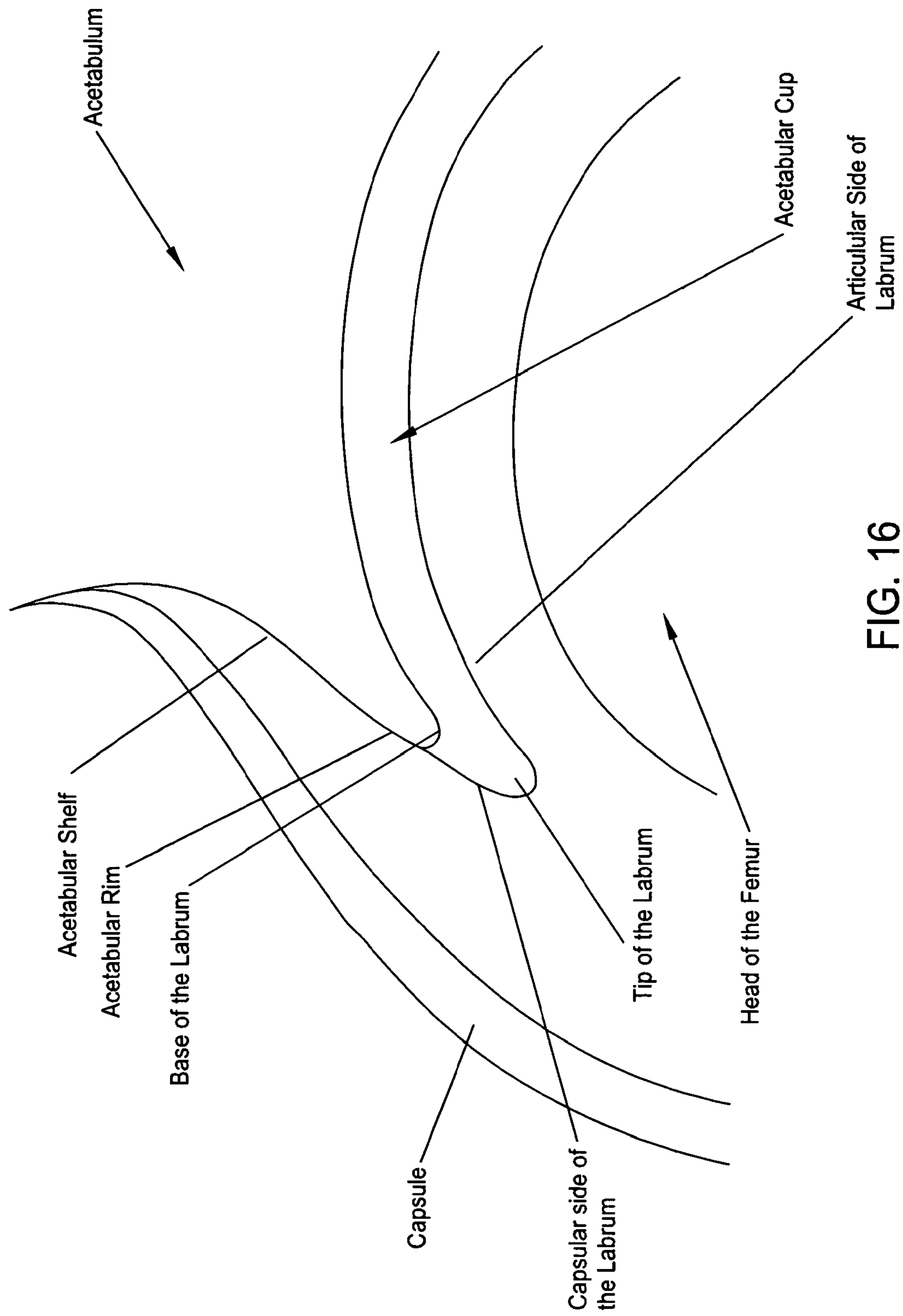
FIG. 16 is a schematic view showing a normal labrum which has its base securely attached to the acetabulum.
Figure 17:
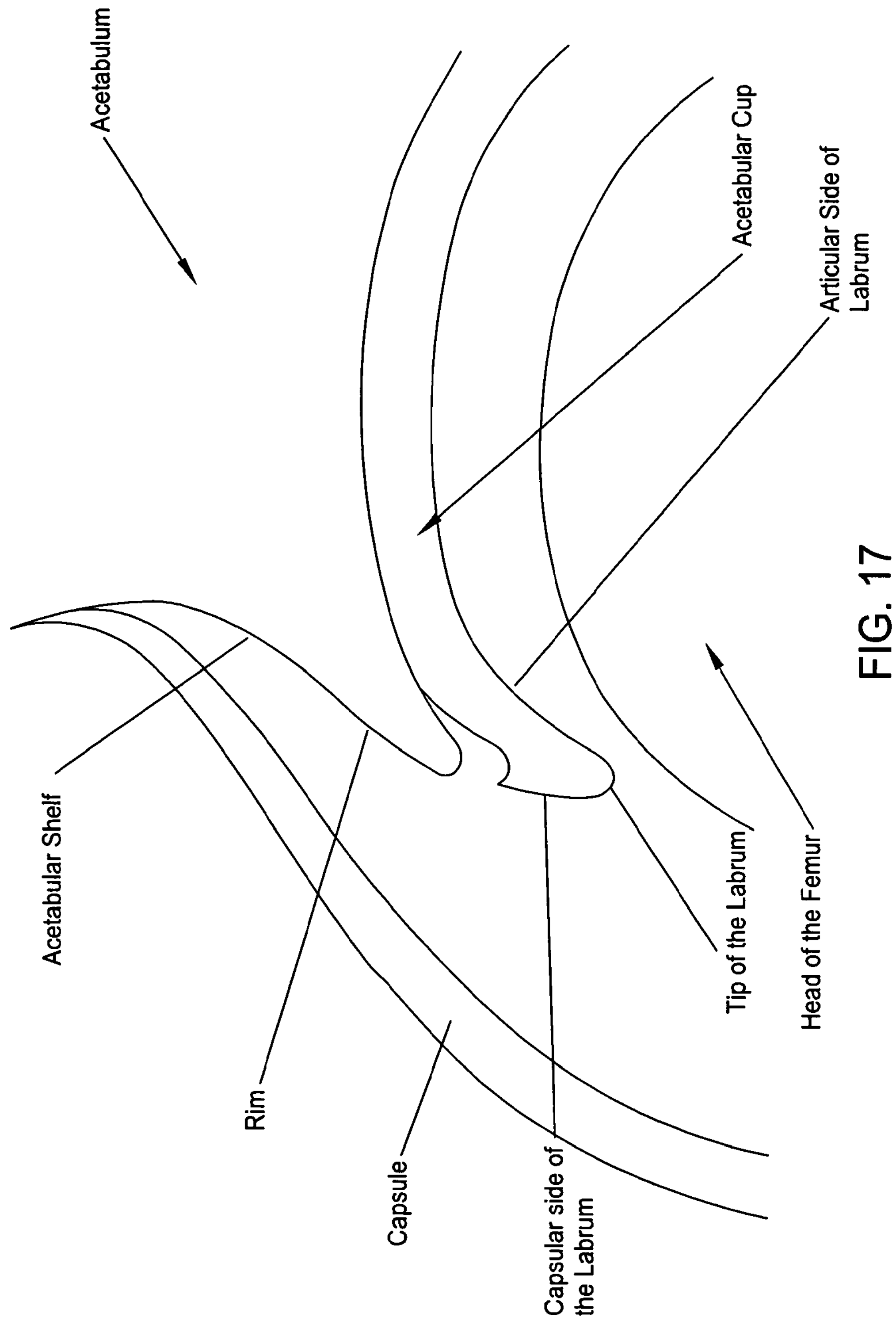
FIG. 17 is a schematic view showing a portion of the labrum detached from the acetabulum.
Figure 18:
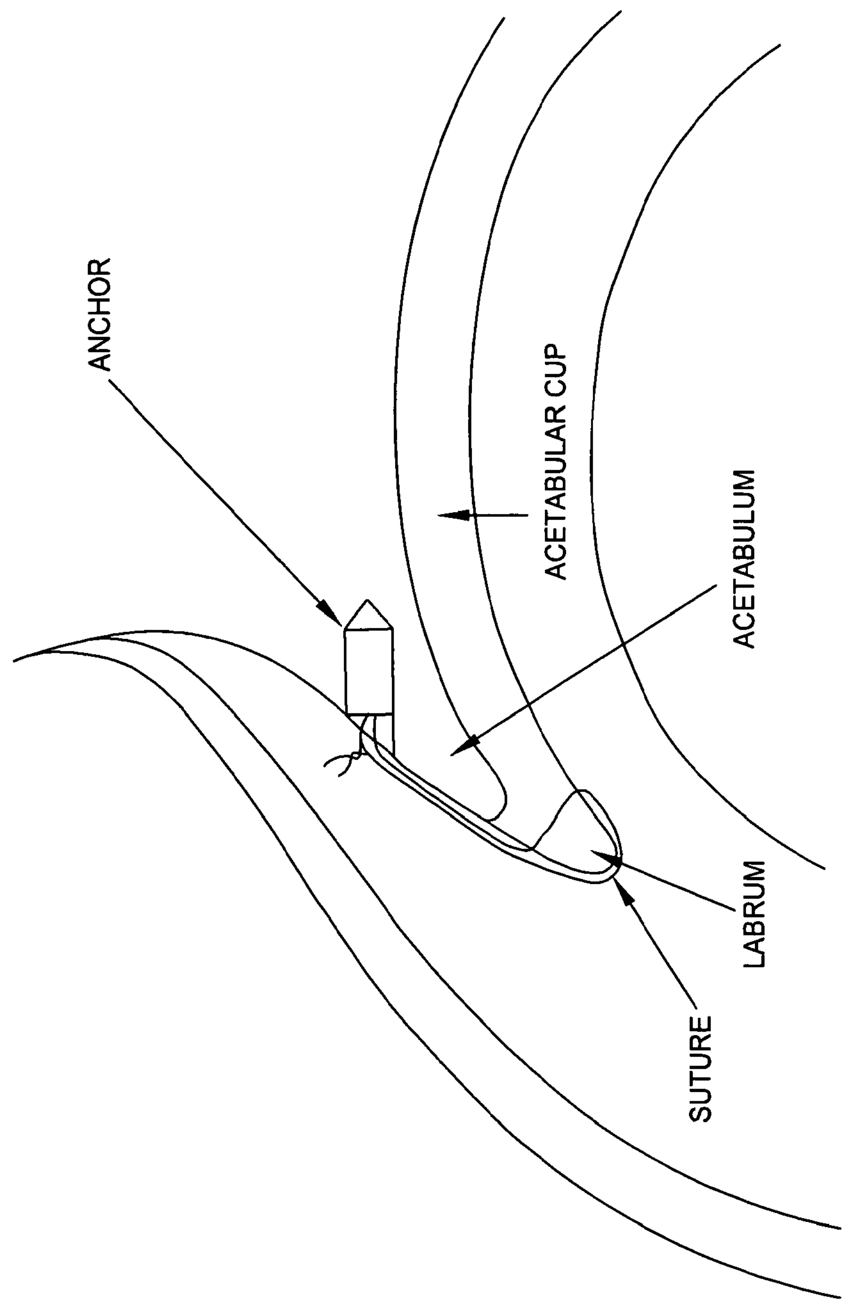
FIG. 18 is a schematic view showing a bone anchor being used to re-attach the labrum to the acetabulum.

As noted above, enlargement 100 may comprise a solid member attached to the distal end of distal loop 95, or it may comprise a suture knot formed by knotting off the distal ends of distal loop 95 of suture 15. In this latter construction, enlargement 100 can be formed out of a single knot or multiple knots. It can be an overhand knot or other knot such as a "Figure 8" knot. Suture 15 can also be heat formed so as to create the enlargement 100. This will create a more rigid feature that better enables movement of enlargement 100 from its distal position to its more proximal position. Such heat forming could also be done on a knot or to seal the suture ends distal to the knot.

Alternative Construction and Method of Use

In one form of the present invention, anchor 10 of suture anchor system 5 may be delivered trans-labrally, i.e., through the labrum and into the acetabular bone, e.g., such as was described above.

In an alternative embodiment of the present invention, anchor 10 may be placed directly into the acetabular bone, without passing through the labrum first, and then suture 15 may be passed through the labrum. In this form of the invention, the components of suture anchor system 5 may remain the same. Alternatively, in this form of the invention, the distal end of hollow guide 25 need not have a sharp tip/edge 136 for penetrating the labrum as described above, and may instead have engagement features for engaging the acetabular bone. One such feature may be a tooth or a plurality of teeth. In this form of the invention, the distal end of the hollow guide may also include a window for confirming that the anchor is properly placed into the bone.

Curved or Angled Configuration and Method of Use

Suture anchor system 5 may also comprise a curved or angled configuration. More particularly, hollow guide 25 may comprise a curve or angle at its distal end. In this form of the invention, the punch (or drill) 30, inserter 20 and anchor 10 are adapted to pass through the curved or angled hollow guide 25 so as to permit a curved or angled delivery of anchor 10.

Use of the Novel Suture Anchor System for Other Tissue Re-Attachment

It should be appreciated that suture anchor system 5 may also be used for re-attaching other soft tissue of the hip joint, or for re-attaching tissue of other joints, or for re-attaching tissue elsewhere in the body. In this respect it should be appreciated that suture anchor system 5 may be used to attach soft tissue to bone or soft tissue to other soft tissue, or for attaching objects (e.g., prostheses) to bone other tissue.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. Apparatus for securing a first object to a second object, the apparatus comprising:

an elongated body having a distal end, a proximal end, and a lumen opening on the proximal end and extending toward the distal end, the lumen comprising a first portion and a second portion, the first portion of the lumen being disposed distal to the second portion of the lumen, and with the first portion of the lumen having a wider diameter than the second portion of the lumen;

at least one slit extending through the side wall of the elongated body and communicating with the lumen, the at least one slit having a distal end and a proximal end, with the distal end of the at least one slit being spaced from the distal end of the elongated body and with the proximal end of the at least one slit being spaced from the proximal end of the elongated body, wherein the at least one slit is not connected to an adjacent slit by a connecting slit; and an elongated element extending through the lumen of the elongated body, the elongated element comprising a proximal end and a distal end and having an enlargement at its distal end, the enlargement having a diameter greater than the second portion of the lumen.

2. Apparatus according to claim 1 wherein at least one of the distal end of the at least one slit and the proximal end of the at least one slit terminates in a relief hole.

3. Apparatus according to claim 1 wherein there are two slits, and further wherein the two slits are on opposite sides of the elongated body.

4. Apparatus according to claim 1 wherein the elongated element comprises a suture.

5. Apparatus according to claim 4 wherein the suture comprises (i) a distal loop connected to the enlargement, and (ii) a proximal loop connected to the distal loop.

6. Apparatus according to claim 5 wherein the distal loop comprises suture of a first maximum width and the proximal loop comprises suture of a second maximum width.

7. Apparatus according to claim 6 wherein the second maximum width is larger than the first maximum width.

8. Apparatus according to claim 5 wherein the distal loop extends out of the lumen of the elongated body, with the distal loop and the elongated body together forming an eyelet.

9. Apparatus according to claim 4 wherein the enlargement comprises a suture knot.

10. Apparatus according to claim 4 wherein the enlargement comprises a solid member and a suture knot, the solid member being disposed proximal to the suture knot.

11. Apparatus according to claim 1 wherein the lumen further comprises a third portion disposed proximal to the second portion of the lumen, the third portion of the lumen having a diameter smaller than the second portion of the lumen.

12. Apparatus according to claim 1 wherein the enlargement is configured to expand the elongated body, and further wherein expansion of the elongated body does not cause the distal end of the elongated body to split open.

13. Apparatus according to claim 1 wherein the enlargement is configured to expand the elongated body, and further wherein expansion of the elongated body does not cause the proximal end of the elongated body to split open.

14. Apparatus according to claim 1 wherein the enlargement is initially at least partially disposed in the first portion of the lumen.

15. Apparatus according to claim 1 wherein the enlargement expands the elongated body when the enlargement is pulled proximally into the second portion of the lumen.

16. Apparatus according to claim 1 wherein the enlargement comprises a solid member.

17. Apparatus according to claim 1 wherein the proximal end of the elongated element extends through the second portion of the lumen of the elongated body and has a maximum width, and further wherein a second elongated element is connected to the elongated element external to the elongated body, the second elongated element having a width, wherein the width of the second elongated element is larger than the maximum width of the proximal end of the elongated element.

18. Apparatus according to claim 1 wherein the distal end of the at least one slit is adjacent to the first portion of the lumen of the elongated body.

19. Apparatus according to claim 18 wherein the proximal end of the at least one slit is proximal to the first portion of the lumen of the elongated body.

20. Apparatus according to claim 1 further comprising an inserter, wherein the elongated body is held to the inserter by applying proximally-directed tension to the elongated element.

21. A method for securing a first object to a second object, the method comprising:

providing apparatus comprising:

an elongated body having a distal end, a proximal end, and a lumen extending between the distal end and the proximal end, the lumen comprising a first portion and a second portion, the first portion of the lumen being disposed distal to the second portion of the lumen, and with the first portion of the lumen having a wider diameter than the second portion of the lumen;

at least one slit extending through the side wall of the elongated body and communicating with the lumen, the at least one slit having a distal end and a proximal end, with the distal end of the at least one slit being spaced from the distal end of the elongated body and with the proximal end of the at least one slit being spaced from the proximal end of the elongated body, wherein the at least one slit is not connected to an adjacent slit by a connecting slit; and an elongated element extending through the lumen of the elongated body, the elongated element comprising a proximal end and a distal end and having an enlargement at its distal end, the enlargement having a diameter greater than the second portion of the lumen;

inserting the elongated body into the second object;

moving the enlargement proximally so as to expand the elongated body; and securing the first object to the second object with the elongated element.

22. Apparatus for securing a first object to a second object, the apparatus comprising:

an elongated body having a distal end, a proximal end, and a lumen opening on the proximal end and extending toward the distal end, the lumen comprising a first portion and a second portion, the first portion of the lumen being disposed distal to the second portion of the lumen, and with the first portion of the lumen having a wider diameter than the second portion of the lumen;

at least one longitudinally-extending slit extending through the side wall of the elongated body and communicating with the lumen, the at least one longitudinally-extending slit having a distal end and a proximal end, with the distal end of the at least one longitudinally-extending slit being spaced from the distal end of the elongated body and with the proximal end of the at least one longitudinally-extending slit being spaced from the proximal end of the elongated body; and an elongated element extending through the lumen of the elongated body, the elongated element comprising a proximal end and a distal end and having an enlargement at its distal end, the enlargement having a diameter greater than the second portion of the lumen;

wherein the elongated element comprises a suture;

wherein the suture comprises (i) a distal loop connected to the enlargement, and (ii) a proximal loop connected to the distal loop;

wherein the distal loop comprises suture of a first diameter and the proximal loop comprises suture of a second diameter.

23. Apparatus according to claim 22 wherein the second diameter is larger than the first diameter.

24. Apparatus according to claim 23 wherein the distal loop is formed out of #2-0 suture and the proximal loop is formed out of #1 suture.

25. Apparatus for securing a first object to a second object, the apparatus comprising:

an elongated body having a distal end, a proximal end, and a lumen opening on the proximal end and extending toward the distal end, the lumen comprising a first portion and a second portion, the first portion of the lumen being disposed distal to the second portion of the lumen, and with the first portion of the lumen having a wider diameter than the second portion of the lumen;

at least two slits extending through the side wall of the elongated body and communicating with the lumen, each of the at least two slits having a distal end and a proximal end, with each of the distal ends of the at least two slits being spaced from the distal end of the elongated body, with each of the proximal ends of the at least two slits being spaced from the proximal end of the elongated body, and the at least two slits being spaced from one another with a portion of the side wall of the elongated body extending therebetween; and an elongated element extending through the lumen of the elongated body, the elongated element comprising a proximal end and a distal end and having an enlargement at its distal end, the enlargement having a diameter greater than the second portion of the lumen;

wherein movement of the enlargement into the second portion of the lumen causes the elongated body to expand, and further wherein the portion of the side wall of the elongated body extending between the at least two slits remains connected to the elongated body distal to the at least two slits and proximal to the at least two slits after expansion of the elongated body.

26. Apparatus according to claim 25 wherein at least one of the distal ends of the at least two slits and the proximal ends of the at least two slits terminates in a relief hole.

27. Apparatus according to claim 25 wherein the at least two slits are on opposite sides of the elongated body.

28. Apparatus according to claim 25 wherein the elongated element comprises a suture.

29. Apparatus according to claim 28 wherein the suture comprises (i) a distal loop connected to the enlargement, and (ii) a proximal loop connected to the distal loop.

30. Apparatus according to claim 29 wherein the distal loop comprises suture of a first maximum width and the proximal loop comprises suture of a second maximum width.

31. Apparatus according to claim 30 wherein the second maximum width is larger than the first maximum width.

32. Apparatus according to claim 29 wherein the distal loop extends out of the lumen of the elongated body, with the distal loop and the elongated body together forming an eyelet.

33. Apparatus according to claim 28 wherein the enlargement comprises a suture knot.

34. Apparatus according to claim 28 wherein the enlargement comprises a solid member and a suture knot, the solid member being disposed proximal to the suture knot.

35. Apparatus according to claim 25 wherein the lumen further comprises a third portion disposed proximal to the second portion of the lumen, the third portion of the lumen having a diameter smaller than the second portion of the lumen.

36. Apparatus according to claim 25 wherein the enlargement is initially at least partially disposed in the first portion of the lumen.

37. Apparatus according to claim 25 wherein expansion of the elongated body does not cause the distal end of the elongated body to split open.

38. Apparatus according to claim 25 wherein expansion of the elongated body does not cause the proximal end of the elongated body to split open.

39. Apparatus according to claim 25 wherein the enlargement comprises a solid member.

40. Apparatus according to claim 25 wherein the proximal end of the elongated element extends through the second portion of the lumen of the elongated body and has a maximum width, and further wherein a second elongated element is connected to the elongated element external to the elongated body, the second elongated element having a width, wherein the width of the second elongated element is larger than the maximum width of the proximal end of the elongated element.

41. Apparatus according to claim 25 wherein the distal ends of the at least two slits are adjacent to the first portion of the lumen of the elongated body.

42. Apparatus according to claim 41 wherein the proximal ends of the at least two slits are proximal to the first portion of the lumen of the elongated body.

43. Apparatus according to claim 25 further comprising an inserter, wherein the elongated body is held to the inserter by applying proximally-directed tension to the elongated element.

44. Apparatus for securing a first object to a second object, the apparatus comprising:

an elongated body having a distal end, a proximal end, and a lumen opening on the proximal end and extending toward the distal end, the lumen comprising a first portion and a second portion, the first portion of the lumen being disposed distal to the second portion of the lumen, and with the first portion of the lumen having a wider diameter than the second portion of the lumen;

at least one slit extending through the side wall of the elongated body and communicating with the lumen, wherein the at least one slit has a distal end and a proximal end, with the distal end of the at least one slit being spaced from the distal end of the elongated body and with the proximal end of the at least one slit being spaced from the proximal end of the elongated body; and an elongated element extending through the lumen of the elongated body, the elongated element comprising a proximal end and a distal end and having an enlargement at its distal end, the enlargement having a diameter greater than the second portion of the lumen;

wherein movement of the enlargement into the second portion of the lumen causes the elongated body to expand, and further wherein during expansion of the elongated body, the side wall of the elongated body expands radially on both sides of the at least one slit.

45. Apparatus according to claim 44 wherein at least one of the distal end of the at least one slit and the proximal end of the at least one slit terminates in a relief hole.

46. Apparatus according to claim 44 wherein there are two slits, and further wherein the two slits are on opposite sides of the elongated body.

47. Apparatus according to claim 44 wherein the elongated element comprises a suture.

48. Apparatus according to claim 47 wherein the suture comprises (i) a distal loop connected to the enlargement, and (ii) a proximal loop connected to the distal loop.

49. Apparatus according to claim 48 wherein the distal loop comprises suture of a first maximum width and the proximal loop comprises suture of a second maximum width.

50. Apparatus according to claim 49 wherein the second maximum width is larger than the first maximum width.

51. Apparatus according to claim 48 wherein the distal loop extends out of the lumen of the elongated body, with the distal loop and the elongated body together forming an eyelet.

52. Apparatus according to claim 47 wherein the enlargement comprises a suture knot.

53. Apparatus according to claim 47 wherein the enlargement comprises a solid member and a suture knot, the solid member being disposed proximal to the suture knot.

54. Apparatus according to claim 44 wherein the lumen further comprises a third portion disposed proximal to the second portion of the lumen, the third portion of the lumen having a diameter smaller than the second portion of the lumen.

55. Apparatus according to claim 44 wherein the enlargement is initially at least partially disposed in the first portion of the lumen.

56. Apparatus according to claim 44 wherein expansion of the elongated body does not cause the distal end of the elongated body to split open.

57. Apparatus according to claim 44 wherein expansion of the elongated body does not cause the proximal end of the elongated body to split open.

58. Apparatus according to claim 44 wherein the enlargement comprises a solid member.

59. Apparatus according to claim 44 wherein the proximal end of the elongated element extends through the second portion of the lumen of the elongated body and has a maximum width, and further wherein a second elongated element is connected to the elongated element external to the elongated body, the second elongated element having a width, wherein the width of the second elongated element is larger than the maximum width of the proximal end of the elongated element.

60. Apparatus according to claim 44 wherein the distal end of the at least one slit is adjacent to the first portion of the lumen of the elongated body.

61. Apparatus according to claim 60 wherein the proximal end of the at least one slit is proximal to the first portion of the lumen of the elongated body.

62. Apparatus according to claim 44 further comprising an inserter, wherein the elongated body is held to the inserter by applying proximally-directed tension to the elongated element.

63. A method for securing a first object to a second object, the method comprising:

providing apparatus comprising:

an elongated body having a distal end, a proximal end, and a lumen opening on the proximal end and extending toward the distal end, the lumen comprising a first portion and a second portion, the first portion of the lumen being disposed distal to the second portion of the lumen, and with the first portion of the lumen having a wider diameter than the second portion of the lumen;

at least two slits extending through the side wall of the elongated body and communicating with the lumen, each of the at least two slits having a distal end and a proximal end, with each of the distal ends of the at least two slits being spaced from the distal end of the elongated body, with each of the proximal ends of the at least two slits being spaced from the proximal end of the elongated body, and the at least two slits being spaced from one another with a portion of the side wall of the elongated body extending therebetween; and an elongated element extending through the lumen of the elongated body, the elongated element comprising a proximal end and a distal end and having an enlargement at its distal end, the enlargement having a diameter greater than the second portion of the lumen;

inserting the elongated body into the second object;

moving the enlargement proximally so as to expand the elongated body, wherein movement of the enlargement into the second portion of the lumen causes the elongated body to expand, and further wherein the portion of the side wall of the elongated body extending between the at least two slits remains connected to the elongated body distal to the at least two slits and proximal to the at least two slits after expansion of the elongated body; and securing the first object to the second object with the elongated element.

64. A method for securing a first object to a second object, the method comprising:

providing apparatus comprising:

an elongated body having a distal end, a proximal end, and a lumen opening on the proximal end and extending toward the distal end, the lumen comprising a first portion and a second portion, the first portion of the lumen being disposed distal to the second portion of the lumen, and with the first portion of the lumen having a wider diameter than the second portion of the lumen;

at least one slit extending through the side wall of the elongated body and communicating with the lumen, wherein the at least one slit has a distal end and a proximal end, with the distal end of the at least one slit being spaced from the distal end of the elongated body and with the proximal end of the at least one slit being spaced from the proximal end of the elongated body; and an elongated element extending through the lumen of the elongated body, the elongated element comprising a proximal end and a distal end and having an enlargement at its distal end, the enlargement having a diameter greater than the second portion of the lumen;

inserting the elongated body into the second object;

moving the enlargement proximally so as to expand the elongated body, wherein movement of the enlargement into the second portion of the lumen causes the elongated body to expand, and further wherein during expansion of the elongated body, the side wall of the elongated body expands radially on both sides of the at least one slit; and securing the first object to the second object with the elongated element.

* * * * *